United States Patent
Widberg et al.

(10) Patent No.: US 10,993,456 B2
(45) Date of Patent: May 4, 2021

(54) OIL BLENDS, PROCESSES FOR THE PREPARATION THEREOF AND THEIR USE IN FORMULAS

(71) Applicant: ENZYMOTEC LTD., Kfar Baruch (IL)

(72) Inventors: Asher Widberg, Haifa (IL); Ran Numa, Haifa (IL); Fabiana Bar-Yoseph, Haifa (IL); Rassan Zuabi, Kfar Neen (IL); Yael Herzog, Gesher HaZiv (IL); Gai Ben-Dror, Gita (IL)

(73) Assignee: ENZYMOTEC LTD., Kfar Baruch (IL)

(*) Notice: Subject to any disclaimer, the term of this patent is extended or adjusted under 35 U.S.C. 154(b) by 0 days.

(21) Appl. No.: 15/679,864

(22) Filed: Aug. 17, 2017

(65) Prior Publication Data

US 2017/0339971 A1 Nov. 30, 2017

Related U.S. Application Data

(63) Continuation of application No. PCT/IL2016/050180, filed on Feb. 16, 2016.

(30) Foreign Application Priority Data

Feb. 17, 2015 (IL) .......................................... 237290

(51) Int. Cl.
*A23D 9/007* (2006.01)
*A23L 33/00* (2016.01)
(Continued)

(52) U.S. Cl.
CPC ............... *A23D 9/007* (2013.01); *A23D 9/04* (2013.01); *A23L 33/11* (2016.08); *A23L 33/40* (2016.08); *A61K 36/28* (2013.01); *A61K 36/286* (2013.01); *A61K 36/31* (2013.01); *A61K 36/48* (2013.01); *A61K 36/889* (2013.01); *C11B 3/12* (2013.01)

(58) Field of Classification Search
CPC ......... A23D 9/007; A23L 33/40; A23L 33/11; C11C 3/08; A61K 2300/00; A61K 36/48; A61K 36/28; A61K 36/286; A61K 36/889; A61K 36/31
See application file for complete search history.

(56) References Cited

U.S. PATENT DOCUMENTS 5,858,449 A 1/1999 Crank et al.
6,057,339 A 5/2000 Gregg
(Continued)

FOREIGN PATENT DOCUMENTS

CA 2642677 A1 * 1/2010
CA 2642677 A1 1/2010
(Continued)

OTHER PUBLICATIONS

Verleyen et al., "Analysis of Free and Esterified Sterols in Vegetable Oils". Journal of American Oil Chemists Society, vol. 79, No. 2. pp. 117-122. (Year: 2002).*

(Continued)

*Primary Examiner* — Erik Kashnikow
*Assistant Examiner* — Assaf Zilbering
(74) *Attorney, Agent, or Firm* — Licata & Tyrrell P.C.

(57) ABSTRACT

The invention provides oil blends, processes for the preparation thereof and their uses.

17 Claims, 3 Drawing Sheets

(51) Int. Cl.
| | |
|---|---|
| A23L 33/11 | (2016.01) |
| C11B 3/12 | (2006.01) |
| A61K 36/889 | (2006.01) |
| A61K 36/28 | (2006.01) |
| A61K 36/31 | (2006.01) |
| A23D 9/04 | (2006.01) |
| A61K 36/286 | (2006.01) |
| A61K 36/48 | (2006.01) |

(56) References Cited

U.S. PATENT DOCUMENTS

| | | |
|---|---|---|
| 8,372,465 B2 | 2/2013 | Nakhasi et al. |
| 2006/0088644 A1 | 4/2006 | Choo et al. |
| 2007/0065541 A1* | 3/2007 | Keller .................... A23C 9/158 426/72 |
| 2007/0218169 A1* | 9/2007 | Meiri-Bendek ........ A23G 3/346 426/72 |
| 2010/0021589 A1 | 1/2010 | Laskov et al. |
| 2010/0178369 A1 | 7/2010 | Arledge et al. |

FOREIGN PATENT DOCUMENTS

| | | |
|---|---|---|
| CN | 1693472 A | 11/2005 |
| EP | 1394144 A1 | 3/2004 |
| GB | 2245812 A | 1/1992 |

OTHER PUBLICATIONS

Martins et al., "Free Fatty Acid Separation From Vegetable Oil Deodorizer Distillate Using Molecular Distillation Process". Separation and Purification Technology 48, pp. 78-84. (Year: 2006).*

Pfrieger, F.W., Role of Cholesterol in Synapse Formation and Function, Biochimica et Biophysica Acta, 2003, 1610(2); pp. 271-280.

Jensen, R.G., Lipids in Human Milk. Lipids, 1999, 34(12); pp. 1243-1271.

Owen, C.G., et al., Infant Feeding and Blood Cholesterol: A Study in Adolescents and a Systematic Review, Pediatrics, 2002, 110(3); pp. 597-608.

Forsyth, J.S., Lipids and Infant Formulas, Nutrition Research Reviews, 1998, 11(2); pp. 255-278.

Decsi, T., et al., Plasma Lipid and Apolipoprotein Concentrations in Full Term Infants Fed Formula Supplemented With Long-Chain Polyunsaturated Fatty Acids and Cholesterol, Eur J Pediatr, 1997, 156(5); pp. 397-400.

Mellies, M.J., et al., Cholesterol, Phytosterols, and Polyunsaturated/Saturated Fatty Acid Ratios During the First 12 Months of Lactation, American Journal of Clinical Nutrition, 1979, 32(12); pp. 2383-2389.

Awad, A.B., et al., Phytosterols as Anticancer Dietary Components: Evidence and Mechanism of Action, Journal of Nutrition, 2000, 130(9); pp. 2127-2130.

Bouic, P.J., Sterols and Sterolins: New Drugs for the Immune System?, Drug Discovery Today, 2002, 7(14); pp. 775-778.

Gordon, H.G., et al., The Effect of Sterols on the Oxidation of Edible Oils, Food Chemistry, 1983, 10; pp. 141-147.

Meshulam, D. et al., Responsiveness of Emulsions Stabilized by Lactoferrin Nanoparticles to Simulated Intestinal Conditions, Food Funct., 2014, 5; pp. 65-73.

Merrill, Li., et al., Oxidative Stability of Conventional and High-Oleic Vegetable Oils with Added Antioxidants, FSTA, (2008), XP002543060, Abstract.

International Search Report for PCT/12016/050180, dated Jul. 27, 2016.

Written Opinion for PCT/IL2016/050180, dated Jul. 27, 2016.

International Preliminary Report on Patentability for PCT/IL2016/050180, dated Aug. 22, 2017.

* cited by examiner

OIL BLENDS, PROCESSES FOR THE PREPARATION THEREOF AND THEIR USE IN FORMULAS

CROSS-REFERENCE TO RELATED APPLICATIONS

This application is a continuation of International Patent Application No. PCT/IL2016/050180, filed Feb. 16, 2016, designating the United States, and claiming benefit of Israel Patent Application No. 237290, filed Feb. 17, 2015, the disclosures of which are incorporated herein by reference in their entirety.

FIELD OF THE INVENTION

This invention relates to the field of oil blends, processes for the preparation thereof and their use in formulas.

BACKGROUND OF THE INVENTION

Cholesterol is a vital compound which serves as essential membrane compound, a cofactor for signaling molecules and precursor for steroid hormones [1]. Human milk is known to be a rich source of cholesterol for the developing infant. The human milk contains substantial cholesterol levels of about 10-20 mg/100 ml at 3 weeks postpartum [2]. This high cholesterol content is correlated with higher plasma cholesterol levels of breastfeeding babies as compared to formula fed babies and may be associated with lower blood cholesterol concentrations in adult life and protection against later development of cardiovascular disease [3].

Cholesterol importance in human milk is evident by the fact that its content is apparently not influenced by dietary manipulation. While maternal dietary and plasma cholesterol levels are closely correlated, breast milk cholesterol levels are not related to those in normal maternal plasma.

Currently marketed infant formulas usually contain blends of vegetable oils and not fats of animal origin, in order to deliver to the infant all required fatty acids. As a result of reducing the use of lipid products from animal sources as ingredients of infant formulas, the formulas usually contain low levels of cholesterol compared to human milk [4].

Due to the importance of cholesterol and its preservation in human milk, attempts have been made to test the effect of its supplementation on formula-fed infants. For example, Decsi et al [5] tested the effect of a formula supplemented with cholesterol on plasma cholesterol levels of full term infants in comparison with a conventional formula. Plasma cholesterol levels on day 5 were significantly higher among the infants who were fed with the cholesterol supplemented infant formula in comparison with infants receiving the conventional formula. In 30 days old infants and thereafter no appreciable effect of diet on plasma cholesterol concentration has been observed.

Plant sterols (PS) or phytosterols such as β-sitosterol, campesterol and stigmasterol occur naturally and are structurally similar to cholesterol, but possess an additional hydrocarbon chain at carbon number 24. Natural occurrence of phytosterols is reported in oil seed as free sterols, esterified forms with fatty acids and phenolic acids, or conjugated with glycosides. Crude food oils derived from soy, corn, sunflower, rapeseed, palm and other crops may contain significant concentrations of phytosterols. Unlike cholesterol, phytosterol concentrations seem to change markedly in human milk depending on the amount of phytosterol in the maternal diet [6].

An area of intense discussion in plant sterol research is the potential bioactive properties of the plant sterols. There is experimental and epidemiological evidence suggesting that plant sterols can protect against certain types of cancer such as colon, breast and prostate, and positive effects on benign prostatic hyperplasia have been reported [7]. The plant sterols activity as immune modulators and their anti-inflammatory properties has also been described [8]. In addition, phytosterols have demonstrated antioxidative capacity [9].

REFERENCES

[1] Pfrieger, F. W., *Role of cholesterol in synapse formation and function.* Biochim Biophys Acta, 2003, 1610(2): p. 271-80.

[2] Jensen, R. G., *Lipids in Human Milk.* Lipids, 1999, 34(12): p. 1243-1271.

[3] Owen, C. G., et al., *Infant feeding and blood cholesterol: a study in adolescents and a systematic review.* Pediatrics, 2002, 110(3): p. 597-608.

[4] Forsyth, J. S., *Lipids and infant formulas.* Nutr Res Rev, 1998, 11(2): p. 255-78.

[5] Decsi, T., M. Fekete, and B. Koletzko, *Plasma lipid and apolipoprotein concentrations in full term infants fed formula supplemented with long-chain polyunsaturated fatty acids and cholesterol.* Eur J Pediatr, 1997, 156(5): p. 397-400.

[6] Mellies, M. J., et al., *Cholesterol, phytosterols, and polyunsaturated/saturated fatty acid ratios during the first 12 months of lactation.* Am J Clin Nutr, 1979, 32(12): p. 2383-9.

[7] Awad, A. B. and C. S. Fink, *Phytosterols as anticancer dietary components: evidence and mechanism of action.* J Nutr, 2000, 130(9): p. 2127-30.

[8] Bouic, P. J., *Sterols and sterolins: new drugs for the immune system?* Drug Discov Today, 2002, 7(14): p. 775-8.

[9] Gordon, H. G. and P. Magos, *The Effect of Sterols on the Oxidation of Edible Oils.* Food Chemistry, 1983, 10: p. 141-147.

[10] Meshulam et al., *Responsiveness of Emulsions Stabilized by Lactoferrin Nano-particles to Simulated Intestinal Conditions"* Food Funct., 2014, 5, 65-73.

SUMMARY OF THE INVENTION

Phytosterols are known to decrease intestinal absorption of cholesterol and as a result reduce cholesterol plasma levels of children and adults. However, since phytosterol levels in human milks are variable and depend on the maternal diet, while cholesterol levels are consistent, and due to the established safety of phytosterols and the potential benefits of their consumption, clinical studies examining the effect of infant formulas on cholesterol homeostasis have focused on the effect of cholesterol supplementation to formulas. The effect of the presence of phytosterols in infant formulas has not been evaluated.

The present invention discloses for the first time oil blends with reduced phytosterol content, particularly for use as the fat ingredient in formulas e.g., infant formulas and baby food.

The present invention thus provides oil blends that comprise oils (e.g., vegetable oils, natural oils, processed vegetable oil or processed oils as herein defined, or any combination of the same) with reduced phytosterol levels compared to the corresponding oils of the same origin, as herein defined. The oil blends are used inter-alia as fat ingredient/s of formulas, e.g. infant formulas and baby food, providing increased plasma cholesterol levels in subjects, e.g. infants, fed with same.

As used herein, the terms "plant sterols", "plant stanols", "phytosterol", "phytosterols", "phytostanol", "phytostanols" or any lingual variations thereof are interchangeable. None limiting examples for phytosterols and phytostanols are: beta-sitosterol, campesterol, brassicasterol, stigmasterol, beta-sitostanol and campestanol.

As used herein, the term "oil blend" refers to a blend of two or more oils. Each one of the oils in the oil blend may be either natural oil or processed oil. The term "oil blend" as used herein is also to be taken to mean a composition essentially comprised of oil blends. It is noted that oil such as naturally occurring oils or processed oils generally comprises substances such as but not limited to triglycerides, diglycerides, monoglycerides, free fatty acids and some other substances such as phospholipids and tocopherols.

As used herein, the term "processed oil" refers to oil which underwent any possible type of process including, but not limited to, a reaction between two or more triglycerides, a reaction between triglycerides and free fatty acids, fractionation and hydrogenation. Non limiting examples of processed oils are Medium Chain Triglyceride (MCT) oil and sn2-palmitate oil.

As used herein the term "MCT oil" refers to an oil which is mainly in the triglyceride form and containing mainly capryc (C8:0) and caprylic (C10:0) fatty acids. The MCT oil may be prepared by an esterification process between glycerol and fatty acids in their free, methyl ester or ethyl ester form.

As used herein the terms "sn2-palmitate", "beta-palmitate", "OPO" and "β-palmitate" are interchangeable and refer to structured triglycerides in which the percentage (level) of palmitic acid moieties at the sn-2 position of the glycerol backbone is at least 33% of the total palmitic acid. The sn2-palmitate may be prepared, for example, by an enzymatic reaction between fatty acid donors (optionally free fatty acids, methyl esters or ethyl esters) containing mainly unsaturated fatty acids and triglycerides containing mainly saturated fatty acids. Preferably both fatty acid donors and triglycerides are derived from vegetable source.

As used herein the term "mainly" is to be understood as constituting at least 50% of the specified feature.

As used herein, the term "vegetable oil" refers to oil from vegetable sources. The vegetable oil may be a natural vegetable oil or a processed oil from vegetable source.

Accordingly, in one of its aspects the present invention provides an oil blend which comprises at least two oils each of which is any one of natural oil or processed oil, wherein at least one of the oils has a reduced phytosterol content that is lower than a pre-determined threshold value corresponding to a nominal value of the phytosterol content of a corresponding oil of same origin.

As used herein, the phrase "corresponding oil of the same origin" refers to either natural or processed oil of the same origin as the oil having reduced phytosterol content, and "same origin" refers to the same oil prior to reducing its phytosterol content. By way of example, the corresponding oil of palm oil with reduced phytosterol content is palm oil before reduction of its phytosterols content.

As used herein, the phrase "pre-determined threshold value corresponding to a nominal value of the phytosterol content of a corresponding oil of the same origin" refers to the phytosterol content of an oil prior to reduction of its phytosterol content. The reduction of phytosterol content below the pre-determined threshold value can be performed prior to or after blending at least two oils.

The pre-determined value may be determined based on known information of the oil or may be determined experimentally. Non-limiting examples of means for use in determining the pre-determined value of the phytosterol includes analytical methods using gas chromatography (GC).

The "phytosterol content" is provided herein in ppm (parts per million) concentration unit. The term "phytosterol content" refers to the total content (the sum) of free phytosterol/s, free phytostanol/s, esterified phytosterols, esterified phytostanols and any other derivatives or form of plant source sterol or stanol in their free form equivalent.

As used herein the terms "phytosterol content", "total amount of phytosterols" or any lingual variations thereof are interchangeable and are to be envisaged as the sum of free phytosterols, free phytostanols, esterified phytosterols, esterified phytostanols and any other derivatives or form of plant source sterol or stanol in their free form equivalent (e.g. for esters, their non-esterified form).

At times, when referring to the ratio between the phytosterol esters content and the free phytosterols content (referred to herein below as "the ratio phytosterol esters:free phytosterols"), the ratio is to be envisaged as the ratio between the phytosterol esters concentration (in ppm) and the free phytosterol concentration (in ppm) i.e., in this case the phytosterol esters are considered as entities different from the free phytosterol and the content of each (i.e., phytosterol esters and free phytosterols) is determined separately.

As used herein, the terms "esterified phytosterols", "esterified phytostanols", "phytosterol esters", "phytostanol esters", "fatty acid phytosterol esters", "fatty acid phytostanol esters" or any lingual variations thereof are interchangeable. The concentration of these esters or esterified species is measured in their free form (i.e., not esterified) equivalents.

As used herein, the term "free form equivalent" refers to the phytosterol component within the phytosterol or phytostanol esters which is in its free form and not in the esterified form.

As used herein the terms "fatty acid phytosterol esters" and "fatty acid phytostanol esters" refers to phytosterol or phytostanol esterified with a fatty acid residue, respectively.

As used herein the term "rapeseed oil" encompasses also canola oil.

In another one of its aspects the present invention provides an oil blend which comprises at least two oils, each of which is any one of a natural oil or processed oil, wherein at least one of the oils is any one of the following oils:

coconut oil having a phytosterol content of less than about 450 ppm;

palm kernel oil having a phytosterol content of less than about 900 ppm;

soybean oil having a phytosterol content of less than about 1800 ppm;

rapeseed oil having a phytosterol content of less than about 5800 ppm;

sunflower oil having a phytosterol content of less than about 1600 ppm;

high oleic sunflower oil having a phytosterol content of less than about 1500 ppm;

corn oil having a phytosterol content of less than about 5900 ppm;

palm olein oil having a phytosterol content of less than about 700 ppm;
palm oil having a phytosterol content of less than about 530 ppm;
safflower oil having a phytosterol content of less than about 8500 ppm;
high oleic safflower oil having a phytosterol content of less than about 1200 ppm;
MCT oil having a phytosterol content of less than about 1000 ppm; or
sn2-palmitate oil having a phytosterol content of less than about 300 ppm.

As used herein the term "about" is to be understood as ±10% of the specified value.

In a further one of its aspects the present invention provides an oil blend which comprises at least two oils, each of which is any one of a natural oil or processed oil, wherein at least one of the oils is any one of the following oils:
coconut oil having a phytosterol content of less than about 450 ppm;
palm kernel oil having a phytosterol content of less than about 900 ppm;
soybean oil having a phytosterol content of less than about 1800 ppm;
rapeseed oil having a phytosterol content of less than about 5800 ppm;
sunflower oil having a phytosterol content of less than about 1600 ppm;
high oleic sunflower oil having a phytosterol content of less than about 1500 ppm;
corn oil having a phytosterol content of less than about 5900 ppm;
palm olein oil having a phytosterol content of less than about 700 ppm;
palm oil having a phytosterol content of less than about 530 ppm;
safflower oil having a phytosterol content of less than about 8500 ppm;
high oleic safflower oil having a phytosterol content of less than about 1200 ppm; or
sn2-palmitate oil having a phytosterol content of less than about 300 ppm.

Yet, in a further one of its aspects the present invention provides a vegetable oil blend which comprises at least two vegetable oils, each of which is any one of natural vegetable oil or processed oil from vegetable source, wherein at least one of the oils has a reduced phytosterol content that is lower than a pre-determined threshold value corresponding to a nominal value of the phytosterol content of a corresponding vegetable oil of same origin.

As used herein the term "vegetable oil blend" refers to a blend/mixture/combination of two or more vegetable oils. Each one of the vegetable oils in the vegetable oil blend may be either natural vegetable oil or processed oil from vegetable source. The term "vegetable oil blend" as used herein is also to be taken to mean a composition essentially comprised of vegetable oil blends. It is noted that vegetable oils such as natural vegetable oil or processed oil from vegetable source generally comprises substances such as but not limited to triglycerides, diglycerides, monoglycerides, free fatty acids and some other substances such as phospholipids and tocopherols.

As used herein the term "processed oil from vegetable source" refers to an oil which underwent any process step provided that most of the triglyceride molecules in said processed oil are essentially the same as those originated from the vegetable source or were produced in a reaction between two or more triglycerides (e.g. interesterification or transesterification of a single vegetable oil or between two or more vegetable oils).

As used herein, the phrase "corresponding vegetable oil of the same origin" refers to either natural or processed vegetable oil of the same origin as the vegetable oil having reduced phytosterol content, and "same origin" refers to the same oil prior to reducing its phytosterol content.

In another one of its aspects the present invention provides a vegetable oil blend which comprises at least two vegetable oils, each of which is any one of natural vegetable oil or processed oil from vegetable source, wherein at least one of the vegetable oils is any one of the following oils:
coconut oil having a phytosterol content of less than about 450 ppm;
palm kernel oil having a phytosterol content of less than about 900 ppm;
soybean oil having a phytosterol content of less than about 1800 ppm;
rapeseed oil having a phytosterol content of less than about 5800 ppm;
sunflower oil having a phytosterol content of less than about 1600 ppm;
high oleic sunflower oil having a phytosterol content of less than about 1500 ppm;
corn oil having a phytosterol content of less than about 5900 ppm;
palm olein oil having a phytosterol content of less than about 700 ppm;
palm oil having a phytosterol content of less than about 530 ppm;
safflower oil having a phytosterol content of less than about 8500 ppm; or
high oleic safflower oil having a phytosterol content of less than about 1200 ppm.

In yet another one of its aspects the present invention provides an oil blend which comprises at least two oils each of which is any one of natural oil or processed oil, wherein at least one of the oils is a specific oil which is any one of coconut oil, palm kernel oil, soybean oil, rapeseed oil, sunflower oil, high oleic sunflower oil, corn oil, palm olein oil, palm oil, safflower oil, high oleic safflower oil, MCT oil or sn2-palmitate oil, wherein the phytosterol content (in ppm) of the total of the specific oils within the blend is below the value obtained using the following formula (I):

$$\left[\sum_{n=1}^{13}(X_n * K_n)\right]/100 \qquad \text{Formula (I)}$$

wherein
n is an integer of 1 to 13 and represents the number of the specific oils;
$X_n$ represents the percent by weight of a specific oil out of the total weight of said n specific oils;
$K_n$ represents a pre-determined threshold value of phytosterol content in ppm of a specific oil;
and wherein said pre-determined threshold value of phytosterol contents of the specific oils ($K_n$) are the following:

| Oil | $K_n$ |
| --- | --- |
| coconut oil | 450 |
| palm kernel oil | 900 |

-continued

| Oil | $K_n$ |
|---|---|
| soybean oil | 1800 |
| rapeseed oil | 5800 |
| sunflower oil | 1600 |
| high oleic sunflower oil | 1500 |
| corn oil | 5900 |
| palm olein oil | 700 |
| palm oil | 530 |
| safflower oil | 8500 |
| high oleic safflower oil | 1200 |
| MCT oil | 1000 |
| sn2-palmitate oil | 300 |

As used herein, "the phytosterol content of the total of the specific oils within the blend" refers to the phytosterol content (in ppm) of the total specific oils comprised within the blend. By way of example, the phytosterol content of the total of the specific oils within a blend which comprises coconut oil and palm oil is the phytosterol content of the total coconut oil and palm oil. If the blend comprises a further non-specific oil (apart from the coconut oil and the palm oil), still, the phytosterol content of the total of the specific oils within a blend is the phytosterol content of the total coconut oil and palm oil (without taking into consideration the phytosterol content of the further non-specific oil).

In another one of its aspects the present invention provides an oil blend which comprises at least two oils each of which is any one of natural oil or processed oil, wherein at least one of the oils is a specific oil which is any one of coconut oil, palm kernel oil, soybean oil, rapeseed oil, sunflower oil, high oleic sunflower oil, corn oil, palm olein oil, palm oil, safflower oil, high oleic safflower oil or sn2-palmitate oil, wherein the phytosterol content in ppm of total said specific oils within the blend is below the value obtained using the following formula (II):

$$\left[\sum_{n=1}^{12}(X_n*K_n)\right]/100 \qquad \text{Formula (II)}$$

wherein
n is an integer of 1 to 12 and represents the number of said specific oils;
$X_n$ represents the percent by weight of a specific oil out of the total weight of said n specific oils;
$K_n$ represents a pre-determined threshold value of phytosterol content in ppm of a specific oil;
and wherein said pre-determined threshold value of phytosterol contents of the specific oils ($K_n$) are the following:

| Oil | $K_n$ |
|---|---|
| coconut oil | 450 |
| palm kernel oil | 900 |
| soybean oil | 1800 |
| rapeseed oil | 5800 |
| sunflower oil | 1600 |
| high oleic sunflower oil | 1500 |
| corn oil | 5900 |
| palm olein oil | 700 |
| palm oil | 530 |
| safflower oil | 8500 |
| high oleic safflower oil | 1200 |
| sn2-palmitate oil | 300 |

Yet, in a further one of its aspects the present invention provides a vegetable oil blend which comprises at least two vegetable oils each of which is any one of natural vegetable oil or processed oil from vegetable source, wherein at least one of the vegetable oils is a specific vegetable oil which is any one of coconut oil, palm kernel oil, soybean oil, rapeseed oil, sunflower oil, high oleic sunflower oil, corn oil, palm olein oil, palm oil, safflower oil or high oleic safflower oil, wherein the phytosterol content in ppm of total said specific oils within the blend is below the value obtained using the following formula (III):

$$\left[\sum_{n=1}^{11}(X_n*K_n)\right]/100 \qquad \text{Formula (III)}$$

wherein
n is an integer of 1 to 11 and represents the number of said specific oils;
$X_n$ represents the percent by weight of a specific oil out of the total weight of said n specific oils;
$K_n$ represents a pre-determined threshold value of phytosterol content in ppm of a specific oil;
and wherein said pre-determined threshold value of phytosterol contents of the specific oils ($K_n$) are the following:

| Oil | $K_n$ |
|---|---|
| coconut oil | 450 |
| palm kernel oil | 900 |
| soybean oil | 1800 |
| rapeseed oil | 5800 |
| sunflower oil | 1600 |
| high oleic sunflower oil | 1500 |
| corn oil | 5900 |
| palm olein oil | 700 |
| palm oil | 530 |
| safflower oil | 8500 |
| high oleic safflower oil | 1200 |

In another one of its aspects the present invention provides an oil blend which comprises at least two oils each of which is any one of natural oil or processed oil, wherein at least one of the oils is any one of:
coconut oil in which the ratio phytosterol esters:free phytosterols is greater than about 0.6;
palm kernel oil in which the ratio phytosterol esters:free phytosterols is greater than about 0.6;
soybean oil in which the ratio phytosterol esters:free phytosterols is greater than about 0.5;
rapeseed oil in which the ratio phytosterol esters:free phytosterols is greater than about 1.7;
sunflower oil in which the ratio phytosterol esters:free phytosterols is greater than about 0.7;
high oleic sunflower oil in which the ratio phytosterol esters:free phytosterols is greater than about 0.7;
corn oil in which the ratio phytosterol esters:free phytosterols is greater than about 1.8;
palm olein oil in which the ratio phytosterol esters:free phytosterols is greater than about 0.4;
palm oil in which the ratio phytosterol esters:free phytosterols is greater than about 1;
safflower oil in which the ratio phytosterol esters:free phytosterols is greater than about 1.1;
high oleic safflower oil in which the ratio phytosterol esters:free phytosterols is greater than about 1.3;

MCT oil in which the ratio phytosterol esters:free phytosterols is greater than about 0.5;
or
sn2-palmitate oil in which the ratio phytosterol esters:free phytosterols is greater than about 0.9.

As used herein, the phrase "the ratio phytosterol esters:free phytosterols" and "the phytosterol esters:free phytosterols ratio" are interchangeable and refer to the ratio between phytosterol esters concentration (in ppm) and free phytosterol concentration (in ppm).

In a further one of its aspects the present invention provides an oil blend which comprises at least two oils each of which is any one of natural oil or processed oil, wherein at least one of the oils is any one of:
coconut oil in which the ratio phytosterol esters:free phytosterols is greater than about 0.6;
palm kernel oil in which the ratio phytosterol esters:free phytosterols is greater than about 0.6;
soybean oil in which the ratio phytosterol esters:free phytosterols is greater than about 0.5;
rapeseed oil in which the ratio phytosterol esters:free phytosterols is greater than about 1.7;
sunflower oil in which the ratio phytosterol esters:free phytosterols is greater than about 0.7;
high oleic sunflower oil in which the ratio phytosterol esters:free phytosterols is greater than 0.7;
corn oil in which the ratio phytosterol esters:free phytosterols is greater than about 1.8;
palm olein oil in which the ratio phytosterol esters:free phytosterols is greater than about 0.4;
palm oil in which the ratio phytosterol esters:free phytosterols is greater than about 1;
safflower oil in which the ratio phytosterol esters:free phytosterols is greater than about 1.1;
high oleic safflower oil in which the ratio phytosterol esters:free phytosterols is greater than about 1.3;
sn2-palmitate oil in which the ratio phytosterol esters:free phytosterols is greater than about 0.9.

In yet a further one of its aspects the present invention provides a vegetable oil blend which comprises at least two oils each of which is any one of natural vegetable oil or processed oil from vegetable source, wherein at least one of the vegetable oils is any one of:
coconut oil in which the ratio phytosterol esters:free phytosterols is greater than about 0.6;
palm kernel oil in which the ratio phytosterol esters:free phytosterols is greater than about 0.6;
soybean oil in which the ratio phytosterol esters:free phytosterols is greater than about 0.5;
rapeseed oil in which the ratio phytosterol esters:free phytosterols is greater than about 1.7;
sunflower oil in which the ratio phytosterol esters:free phytosterols is greater than about 0.7;
high oleic sunflower oil in which the ratio phytosterol esters:free phytosterols is greater than about 0.7;
corn oil in which the ratio phytosterol esters:free phytosterols is greater than about 1.8;
palm olein oil in which the ratio phytosterol esters:free phytosterols is greater than about 0.4;
palm oil in which the ratio phytosterol esters:free phytosterols is greater than about 1;
safflower oil in which the ratio phytosterol esters:free phytosterols is greater than about 1.1; or
high oleic safflower oil in which the ratio phytosterol esters:free phytosterols is greater than about 1.3.

Yet, in a further one of its aspects the present invention provides an oil blend which comprises at least two oils, each of which is any one of natural oil or processed oil, wherein at least one of the oils is a specific oil which is any one of coconut oil, palm kernel oil, soybean oil, rapeseed oil, sunflower oil, high oleic sunflower oil, corn oil, palm olein oil, palm oil, safflower oil, high oleic safflower oil, MCT oil or sn2-palmitate oil, wherein the ratio between phytosterol esters concentration in ppm and free phytosterols concentration in ppm in total said specific oils within the blend is above the result obtained using the following formula (IV):

$$0.01 * \left[\sum_{n=1}^{13} (X_n * R_n * K_n)\right] / \left[\sum_{n=1}^{13} (K_n)\right] \qquad \text{Formula (IV)}$$

wherein
n is an integer of 1 to 13 and represents the number of said specific oils;
$X_n$ represents the percent by weight of a specific oil out of the total weight of said n specific oils;
$R_n$ represents a pre-determined threshold value of the ratio between the phytosterol esters concentration (in ppm) and the free phytosterol concentration (in ppm) in the specific oil;
$K_n$ represents a pre-determined threshold value of phytosterol content in ppm of said specific oil;
and wherein the pre-determined threshold value of the ratio between phytosterol esters concentration in ppm and free phytosterols concentration in ppm in the specific oils ($R_n$) are the following:

| Oil | $R_n$ |
| --- | --- |
| coconut oil | 0.6 |
| palm kernel oil | 0.6 |
| soybean oil | 0.5 |
| rapeseed oil | 1.7 |
| sunflower oil | 0.7 |
| high oleic sunflower oil | 0.7 |
| corn oil | 1.8 |
| palm olein oil | 0.4 |
| palm oil | 1 |
| safflower oil | 1.1 |
| high oleic safflower oil | 1.3 |
| MCT oil | 0.5 |
| sn2-palmitate oil | 0.9 | and wherein the pre-determined threshold value of phytosterol contents of the specific oils ($K_n$) are the following:

| Oil | $K_n$ |
| --- | --- |
| coconut oil | 450 |
| palm kernel oil | 900 |
| soybean oil | 1800 |
| rapeseed oil | 5800 |
| sunflower oil | 1600 |
| high oleic sunflower oil | 1500 |
| corn oil | 5900 |
| palm olein oil | 700 |
| palm oil | 530 |
| safflower oil | 8500 |
| high oleic safflower oil | 1200 |
| MCT oil | 1000 |
| sn2-palmitate oil | 300 |

In another one of its aspects the present invention provides an oil blend which comprises at least two oils, each of which is any one of natural oil or processed oil, wherein at least one of the oils is a specific oil which is any one of coconut oil, palm kernel oil, soybean oil, rapeseed oil, sunflower oil, high oleic sunflower oil, corn oil, palm olein oil, palm oil, safflower oil, high oleic safflower oil or sn2-palmitate oil, wherein the ratio between phytosterol esters concentration in ppm and free phytosterols concentration in ppm in total said specific oils within the blend is above the result obtained using the following formula (V):

$$0.01 * \left[\sum_{n=1}^{12} (X_n * R_n * K_n)\right] \Big/ \left[\sum_{n=1}^{12} (K_n)\right] \quad \text{Formula (V)}$$

wherein
n is an integer of 1 to 12 and represents the number of said specific oils;
$X_n$ represents the percent by weight of a specific oil out of the total weight of said n specific oils;
$R_n$ represents a pre-determined threshold value of the ratio between the phytosterol esters concentration (in ppm) and the free phytosterol concentration (in ppm) in the specific oil;
$K_n$ represents a pre-determined threshold value of the phytosterol content in ppm of said specific oil;
and wherein the pre-determined threshold value of the ratio between phytosterol esters concentration in ppm and free phytosterols concentration in ppm in the specific oils ($R_n$) are the following:

| Oil | $R_n$ |
| --- | --- |
| coconut oil | 0.6 |
| palm kernel oil | 0.6 |
| soybean oil | 0.5 |
| rapeseed oil | 1.7 |
| sunflower oil | 0.7 |
| high oleic sunflower oil | 0.7 |
| corn oil | 1.8 |
| palm olein oil | 0.4 |
| palm oil | 1 |
| safflower oil | 1.1 |
| high oleic safflower oil | 1.3 |
| sn2-palmitate oil | 0.9 | and wherein said pre-determined threshold value of the phytosterol contents of the specific oils ($K_n$) are the following:

| Oil | $K_n$ |
| --- | --- |
| coconut oil | 450 |
| palm kernel oil | 900 |
| soybean oil | 1800 |
| rapeseed oil | 5800 |
| sunflower oil | 1600 |
| high oleic sunflower oil | 1500 |
| corn oil | 5900 |
| palm olein oil | 700 |
| palm oil | 530 |
| safflower oil | 8500 |
| high oleic safflower oil | 1200 |
| sn2-palmitate oil | 300 |

Yet, in a further one of its aspects the present invention provides a vegetable oil blend which comprises at least two vegetable oils, each of which is any one of natural vegetable oil or processed oil from vegetable source, wherein at least one of the vegetable oils is a specific oil which is any one of coconut oil, palm kernel oil, soybean oil, rapeseed oil, sunflower oil, high oleic sunflower oil, corn oil, palm olein oil, palm oil, safflower oil or high oleic safflower oil, wherein the ratio between phytosterol esters concentration in ppm and free phytosterols concentration in ppm in total said specific oils within the blend is above the result obtained using the following formula (VI):

$$0.01 * \left[\sum_{n=1}^{11} (X_n * R_n * K_n)\right] \Big/ \left[\sum_{n=1}^{11} (K_n)\right] \quad \text{Formula (VI)}$$

wherein
n is an integer of 1 to 11 and represents the number of said specific oils;
$X_n$ represents the percent by weight of a specific oil out of the total weight of said n specific oils;
$R_n$ represents a pre-determined threshold value of the ratio between the phytosterol esters concentration (in ppm) and the free phytosterol concentration (in ppm) in the specific oil;
$K_n$ represents a pre-determined threshold value of phytosterol content in ppm of said specific oil;
and wherein the pre-determined threshold value of the ratio between phytosterol esters concentration in ppm and free phytosterols concentration in ppm in the specific oils ($R_n$) are the following:

| Oil | $R_n$ |
| --- | --- |
| coconut oil | 0.6 |
| palm kernel oil | 0.6 |
| soybean oil | 0.5 |
| rapeseed oil | 1.7 |
| sunflower oil | 0.7 |
| high oleic sunflower oil | 0.7 |
| corn oil | 1.8 |
| palm olein oil | 0.4 |
| palm oil | 1 |
| safflower oil | 1.1 |
| high oleic safflower oil | 1.3 | and wherein said pre-determined threshold value of the phytosterol contents of the specific oils ($K_n$) are the following:

| Oil | $K_n$ |
| --- | --- |
| coconut oil | 450 |
| palm kernel oil | 900 |
| soybean oil | 1800 |
| rapeseed oil | 5800 |
| sunflower oil | 1600 |
| high oleic sunflower oil | 1500 |
| corn oil | 5900 |
| palm olein oil | 700 |
| palm oil | 530 |
| safflower oil | 8500 |
| high oleic safflower oil | 1200 |

In another one of its aspects the present invention provides an oil blend which contains a total amount of phytosterols of at most about 4000 ppm.

In yet another one of its aspects the present invention provides a vegetable oil blend which contains a total amount of phytosterols of at most about 4000 ppm.

In a further one of its aspects the present invention provides oil blends as herein disclosed wherein the oil blends have an endogenic tocopherol (TCP) concentration of at most about 800 ppm.

In yet a further one of its aspects the present invention provides vegetable oil blends as herein disclosed wherein the vegetable oil blends have an endogenous tocopherol concentration of at most about 800 ppm.

As used herein, the term "endogenous tocopherol concentration" refers to tocopherol levels which are extracted from the oil source without the external addition of natural or synthetic tocopherols.

In another one of its aspects the present invention provides an oil blend which consists at least one vegetable oil and at least one of MCT oil and sn2-palmitate oil wherein in the blend the total amount of phytosterols is at most about 4000 ppm.

In another one of its aspects the present invention provides nutritional compositions, pharmaceutical compositions, nutraceutical compositions, parenteral nutrition compositions, functional food or medical food comprising an oil blend (e.g., vegetable oil blend) according to the invention for use in enteral or parenteral preparations for administration to a subject.

In another one of its aspects the present invention provides a formula, an infant formula, parenteral formula, baby food, toddler formula, child formula or adult formula comprising any one of the oil blends (e.g., vegetable oil blends) according to the present invention.

As used herein the terms "parenteral formula" and "parenteral nutrition composition" or any lingual variations thereof are envisaged as being applicable for administration to a subject body via a route different from the digestive system and may supply part or all of the daily nutritional requirements. Non limiting examples of such administration are via intravenous, total parenteral nutrition (TPN), partial parenteral nutrition, total nutrient admixture (TNA), partial nutrient admixture, peripheral parenteral nutrition (PPN) routes, etc. Other parenteral routes of administration may be intramuscular, intraperitoneal, subcutaneous administrations, etc.

In another one of its aspects the present invention provides a process for the preparation of oil blends according to the invention, the process comprises providing one or more means for reducing the phytosterol content of at least one oil and mixing the resulted oil with reduced phytosterol content with at least one other oil to thereby obtain an oil blend with reduced phytosterol content.

In a further one of its aspects the present invention provides a process for the preparation of oil blends according to the invention, the process comprises mixing at least two oils, providing one or more means for reducing the phytosterol content of the resulted mixture of the oils to thereby obtain an oil blend with reduced phytosterol content.

In another one of its aspects the present invention provides a process for the preparation of vegetable oil blends according to the invention, the process comprises providing one or more means for reducing the phytosterol content of at least one vegetable oil and mixing the resulted oil with reduced phytosterol content with at least one other vegetable oil to thereby obtain a vegetable oil blend with reduced phytosterol content.

In a further one of its aspects the present invention provides a process for the preparation of vegetable oil blends according to the invention, the process comprises mixing at least two vegetable oils, providing one or more means for reducing the phytosterol content of the resulted mixture of the vegetable oils to thereby obtain a vegetable oil blend with reduced phytosterol content.

In a further one of its aspects the present invention provides a process for the preparation of oil blends according to the invention, the process comprises providing one or more means for reducing the phytosterol content of at least one oil and mixing the at least one oil with reduced phytosterol content with at least one other oil which underwent a process for phytosterol reduction, to thereby obtain an oil blend with reduced phytosterol content.

In yet a further one of its aspects the present invention provides a process for the preparation of vegetable oil blends according to the invention, the process comprises providing one or more means for reducing the phytosterol content of at least one vegetable oil and mixing the at least one vegetable oil with reduced phytosterol content with at least one other vegetable oil which underwent a process for phytosterol reduction, to thereby obtain a vegetable oil blend with reduced phytosterol content.

In yet a further one of its aspects the present invention provides a process for the preparation of an oil with reduced phytosterol content, the process comprises one or more means for reducing the phytosterol content of the oil during the extraction of the oil from oil-containing natural sources such as seeds and beans.

In another one of its aspects the present invention provides a process for reducing phytosterol content in an oil (e.g., vegetable oil), the process comprises subjecting the oil to molecular distillation in a distillation system, wherein the molecular distillation is performed under specific temperature and vacuum conditions, and wherein the weight percentage of the oil distillate resulting from the molecular distillation is between about 2% to about 60% out of the total weight of the oil subjected to the molecular distillation.

In a further one of its aspects the present invention provides a process for the preparation of an oil blend which comprises at least two oils wherein at least one of the oils has reduced phytosterol content, the process comprising:

subjecting at least one oil to molecular distillation in a distillation system, wherein the molecular distillation is performed under specific temperature and vacuum conditions, and wherein the weight percentage of the at least one oil distillate resulting from the molecular distillation is between about 2% to about 60% out of the total weight of the at least one oil subjected to the molecular distillation; and blending the at least one distilled oil with at least one other oil, wherein the at least one other oil is optionally also subjected to the molecular distillation;

to thereby obtain an oil blend with reduced phytosterol content.

Yet, in another one of its aspects the present invention provides a process for the preparation of an oil blend having reduced phytosterol content, the process comprises:

mixing at least two oils;

subjecting the at least two oils to molecular distillation in a distillation system, wherein the molecular distillation is performed under specific temperature and vacuum conditions, and wherein the weight percentage of the at least two oils distillate resulting from the molecular distillation is between about 2% to about 60% out of the total weight of the at least two oils subjected to the molecular distillation; and optionally blending the resulted at least two oils with reduced phytosterol content with at least one further oil wherein the at least one further oil is optionally also subjected to said molecular distillation;

to thereby obtain an oil blend with reduced phytosterol content.

Yet, in a further one of its aspects the present invention provides a process for the preparation of oil blends as herein disclosed for use as lipid ingredients in formulas such as infant formula.

In a further one of its aspects the present invention provides oil blends as herein disclosed for use as lipid ingredients in formulas such as infant formula.

In a further one of its aspects the present invention provides oil blends as herein disclosed for use as lipid ingredients in nutritional compositions, pharmaceutical compositions, nutraceutical compositions, parenteral nutrition compositions, functional food or medical food.

In a further one of its aspects the present invention provides oil blends as herein disclosed for use in the preparation of nutritional compositions, pharmaceutical compositions, nutraceutical compositions, parenteral nutrition compositions, functional food or medical food.

In yet a further one of its aspects the present invention provides phytosterols obtained in the processes disclosed herein.

The invention further provides various uses of oil blends according to the invention as well as various methods utilizing oil blends according to the invention. Various uses and methods are detailed herein below.

Thus, the present invention provides oil blends according to the invention for use in improving certain parameters and/or conditions in a subject as detailed herein below. The present invention further provides methods for improving certain parameters and/or conditions in a subject as detailed herein below. The methods comprise administering oil blends according to the invention to a subject.

BRIEF DESCRIPTION OF THE DRAWINGS

In order to understand the invention and to see how it may be carried out in practice, embodiments will now be described, by way of non-limiting examples only, with reference to the accompanying drawings, in which.

DETAILED DESCRIPTION OF THE INVENTION

Figure 1:
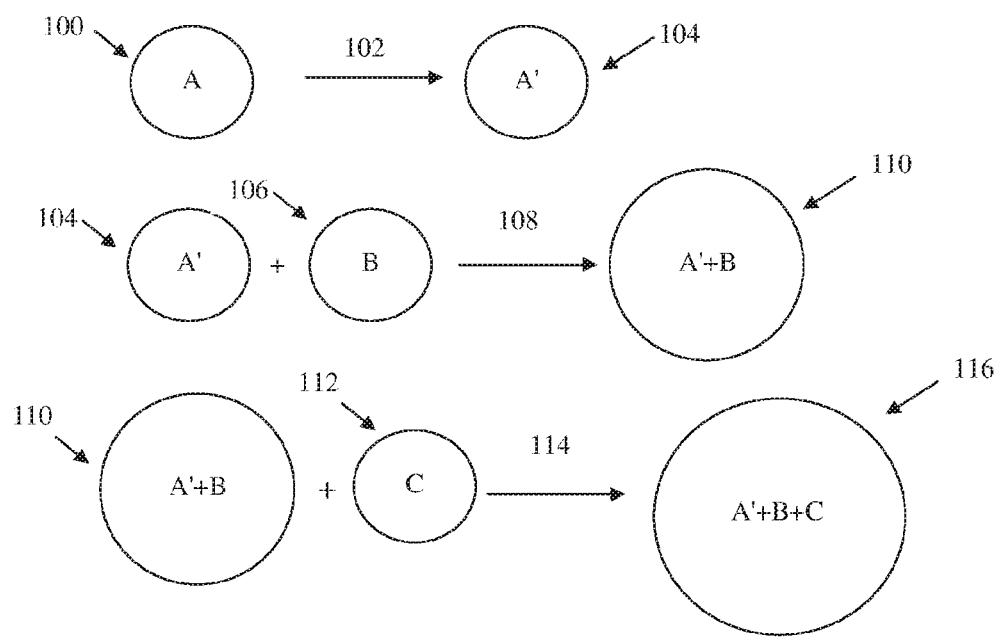
FIG. 1 illustrates an embodiment of the invention according to which the phytosterol content of one specific oil is reduced prior to blending with second specific oil.

In one of its aspects the present invention provides an oil blend which comprises at least two oils each of which is any one of natural oil or processed oil, wherein at least one of the oils has a reduced phytosterol content that is lower than a pre-determined threshold value corresponding to a nominal value of the phytosterol content of a corresponding oil of same origin.

In some embodiments the at least one oil having a reduced phytosterol content is coconut oil which has a phytosterol content that is lower than a pre-determined threshold value of about 450 ppm.

In some embodiments the at least one oil having a reduced phytosterol content is palm kernel oil which has a phytosterol content that is lower than a pre-determined threshold value of about 900 ppm.

In some embodiments the at least one oil having a reduced phytosterol content is soybean oil which has a phytosterol content that is lower than a pre-determined threshold value of about 1800 ppm.

In some embodiments the at least one oil having a reduced phytosterol content is rapeseed oil which has a phytosterol content that is lower than a pre-determined threshold value of about 5800 ppm.

In some embodiments the at least one oil having a reduced phytosterol content is sunflower oil which has a phytosterol content that is lower than a pre-determined threshold value of about 1600 ppm.

In some embodiments the at least one oil having a reduced phytosterol content is high oleic sunflower oil which has a phytosterol content that is lower than a pre-determined threshold value of about 1500 ppm.

In some embodiments the at least one oil having a reduced phytosterol content is corn oil which has a phytosterol content that is lower than a pre-determined threshold value of about 5900 ppm.

In some embodiments the at least one oil having a reduced phytosterol content is palm olein oil which has a phytosterol content that is lower than a pre-determined threshold value of about 700 ppm.

In some embodiments the at least one oil having a reduced phytosterol content is palm oil which has a phytosterol content that is lower than a pre-determined threshold value of about 530 ppm.

In some embodiments the at least one oil having a reduced phytosterol content is safflower oil which has a phytosterol content that is lower than a pre-determined threshold value of about 8500 ppm.

In some embodiments the at least one oil having a reduced phytosterol content is high oleic safflower oil which has a phytosterol content that is lower than a pre-determined threshold value of about 1200 ppm.

In some embodiments the at least one oil having a reduced phytosterol content is MCT oil which has a phytosterol content that is lower than a pre-determined threshold value of about 1000 ppm.

In some embodiments the at least one oil having a reduced phytosterol content is sn2-palmitate oil which has a phytosterol content that is lower than a pre-determined threshold value of about 300 ppm.

In some embodiments the at least one oil is a coconut oil having a phytosterol esters: free phytosterols ratio that is greater than about 0.6.

In some embodiments the at least one oil is a palm kernel oil having a phytosterol esters:free phytosterols ratio that is greater than about 0.6.

In some embodiments the at least one oil is a soybean oil having a phytosterol esters: free phytosterols ratio that is greater than about 0.5.

In some embodiments the at least one oil is a rapeseed oil having a phytosterol esters: free phytosterols ratio that is greater than about 1.7.

In some embodiments the at least one oil is a sunflower oil having a phytosterol esters: free phytosterols ratio that is greater than about 0.7.

In some embodiments the at least one oil is a high oleic sunflower oil having a phytosterol esters:free phytosterols ratio that is greater than about 0.7.

In some embodiments the at least one oil is a corn oil having a phytosterol esters:free phytosterols ratio that is greater than about 1.8.

In some embodiments the at least one oil is a palm olein oil having a phytosterol esters: free phytosterols ratio that is greater than about 0.4.

In some embodiments the at least one oil is a palm oil having a phytosterol esters:free phytosterols ratio that is greater than about 1.

In some embodiments the at least one oil is a safflower oil having a phytosterol esters: free phytosterols ratio that is greater than about 1.1.

In some embodiments the at least one oil is a high oleic safflower oil having a phytosterol esters:free phytosterols ratio that is greater than about 1.3.

In some embodiments the at least one oil is a MCT oil having a phytosterol esters:free phytosterols ratio that is greater than about 0.5.

In some embodiments the at least one oil is sn2-palmitate oil having a phytosterol esters:free phytosterols ratio that is greater than about 0.9.

In another one of its aspects the present invention provides an oil blend which comprises at least two oils, each of which is any one of a natural oil or processed oil, wherein at least one of the oils is any one of the following oils:

coconut oil having a phytosterol content of less than about 450 ppm;

palm kernel oil having a phytosterol content of less than about 900 ppm;

soybean oil having a phytosterol content of less than about 1800 ppm;

rapeseed oil having a phytosterol content of less than about 5800 ppm;

sunflower oil having a phytosterol content of less than about 1600 ppm;

high oleic sunflower oil having a phytosterol content of less than about 1500 ppm;

corn oil having a phytosterol content of less than about 5900 ppm;

palm olein oil having a phytosterol content of less than about 700 ppm;

palm oil having a phytosterol content of less than about 530 ppm;

safflower oil having a phytosterol content of less than about 8500 ppm;

high oleic safflower oil with a phytosterol content of less than about 1200 ppm;

MCT oil having a phytosterol content of less than about 1000 ppm; or sn2-palmitate oil having a phytosterol content of less than about 300 ppm.

It is noted that any one or more than one of the above listed oils can be included in the blend. In addition, the blend can also comprise other, non-listed oils with reduced phytosterol content (compared to the corresponding oil of same origin). Further, the blend can also comprise other non-listed oils e.g., with no reduced phytosterol content.

In a further one of its aspects the present invention provides an oil blend which comprises at least two oils, each of which is any one of a natural oil or processed oil, wherein at least one of the oils is any one of the following oils:

coconut oil having a phytosterol content of less than about 450 ppm;

palm kernel oil having a phytosterol content of less than about 900 ppm;

soybean oil having a phytosterol content of less than about 1800 ppm;

rapeseed oil having a phytosterol content of less than about 5800 ppm;

sunflower oil having a phytosterol content of less than about 1600 ppm;

high oleic sunflower oil having a phytosterol content of less than about 1500 ppm;

corn oil having a phytosterol content of less than about 5900 ppm;

palm olein oil having a phytosterol content of less than about 700 ppm;

palm oil having a phytosterol content of less than about 530 ppm;

safflower oil having a phytosterol content of less than about 8500 ppm;

high oleic safflower oil having a phytosterol content of less than about 1200 ppm; or sn2-palmitate oil having a phytosterol content of less than about 300 ppm.

It is noted that any one or more than one of the above listed oils can be included in the blend. In addition, the blend can also comprise other, non-listed oils with reduced phytosterol content (compared to the corresponding oil of same origin). Further, the blend can also comprise other non-listed oils e.g., with no reduced phytosterol content.

Yet, in a further one of its aspects the present invention provides a vegetable oil blend which comprises at least two vegetable oils, each of which is any one of natural vegetable oil or processed oil from vegetable source, wherein at least one of the oils has a reduced phytosterol content that is lower than a pre-determined threshold value corresponding to a nominal value of the phytosterol content of a corresponding vegetable oil of same origin.

In some embodiments the at least one vegetable oil having a reduced phytosterol content is coconut oil which has a phytosterol content that is lower than a pre-determined threshold value of about 450 ppm.

In some embodiments the at least one vegetable oil having a reduced phytosterol content is palm kernel oil which has a phytosterol content that is lower than a pre-determined threshold value of about 900 ppm.

In some embodiments the at least one vegetable oil having a reduced phytosterol content is soybean oil which has a phytosterol content that is lower than a pre-determined threshold value of about 1800 ppm.

In some embodiments the at least one vegetable oil having a reduced phytosterol content is rapeseed oil which has a phytosterol content that is lower than a pre-determined threshold value of about 5800 ppm.

In some embodiments the at least one vegetable oil having a reduced phytosterol content is sunflower oil which has a phytosterol content that is lower than a pre-determined threshold value of about 1600 ppm.

In some embodiments the at least one vegetable oil having a reduced phytosterol content is high oleic sunflower oil which has a phytosterol content that is lower than a pre-determined threshold value of about 1500 ppm.

In some embodiments the at least one vegetable oil having a reduced phytosterol content is corn oil which has a phytosterol content that is lower than a pre-determined threshold value of about 5900 ppm.

In some embodiments the at least one vegetable oil having a reduced phytosterol content is palm olein oil which has a phytosterol content that is lower than a pre-determined threshold value of about 700 ppm.

In some embodiments the at least one vegetable oil having a reduced phytosterol content is palm oil which has a phytosterol content that is lower than a pre-determined threshold value of about 530 ppm.

In some embodiments the at least one vegetable oil having a reduced phytosterol content is safflower oil which has a phytosterol content that is lower than a pre-determined threshold value of about 8500 ppm.

In some embodiments the at least one vegetable oil having a reduced phytosterol content is high oleic safflower oil which has a phytosterol content that is lower than a pre-determined threshold value of about 1200 ppm.

In some embodiments the at least one vegetable oil is a coconut oil having a phytosterol esters:free phytosterols ratio that is greater than about 0.6.

In some embodiments the at least one vegetable oil is a palm kernel oil having a phytosterol esters:free phytosterols ratio that is greater than about 0.6.

In some embodiments the at least one vegetable oil is a soybean oil having a phytosterol esters:free phytosterols ratio that is greater than about 0.5.

In some embodiments the at least one vegetable oil is a rapeseed oil having a phytosterol esters:free phytosterols ratio that is greater than about 1.7.

In some embodiments the at least one vegetable oil is a sunflower oil having a phytosterol esters:free phytosterols ratio that is greater than about 0.7.

In some embodiments the at least one vegetable oil is a high oleic sunflower oil having a phytosterol esters:free phytosterols ratio that is greater than about 0.7.

In some embodiments the at least one vegetable oil is a corn oil having a phytosterol esters:free phytosterols ratio that is greater than about 1.8.

In some embodiments the at least one oil is a palm olein oil having a phytosterol esters: free phytosterols ratio that is greater than about 0.4.

In some embodiments the at least one vegetable oil is a palm oil having a phytosterol esters:free phytosterols ratio that is greater than about 1.

In some embodiments the at least one vegetable oil is a safflower oil having a phytosterol esters:free phytosterols ratio that is greater than about 1.1.

In some embodiments the at least one vegetable oil is a high oleic safflower oil having a phytosterol esters:free phytosterols ratio that is greater than about 1.3.

In another one of its aspects the present invention provides a vegetable oil blend which comprises at least two vegetable oils, each of which is any one of natural vegetable oil or processed oil from vegetable source, wherein at least one of the vegetable oils is any one of the following oils:

coconut oil having a phytosterol content of less than about 450 ppm;

palm kernel oil having a phytosterol content of less than about 900 ppm;

soybean oil having a phytosterol content of less than about 1800 ppm;

rapeseed oil having a phytosterol content of less than about 5800 ppm;

sunflower oil having a phytosterol content of less than about 1600 ppm;

high oleic sunflower oil having a phytosterol content of less than about 1500 ppm;

corn oil having a phytosterol content of less than about 5900 ppm;

palm olein oil having a phytosterol content of less than about 700 ppm;

palm oil having a phytosterol content of less than about 530 ppm;

safflower oil having a phytosterol content of less than about 8500 ppm; or high oleic safflower oil having a phytosterol content of less than about 1200 ppm.

It is noted that any one or more than one of the above listed vegetable oils can be included in the blend. In addition, the blend can also comprise other, non-listed vegetable oils with reduced phytosterol content (compared to the corresponding oil of same origin). Further, the blend can also comprise other non-listed vegetable oils e.g., with no reduced phytosterol content.

In yet another one of its aspects the present invention provides an oil blend which comprises at least two oils each of which is any one of natural oil or processed oil, wherein at least one of the oils is a specific oil which is any one of coconut oil, palm kernel oil, soybean oil, rapeseed oil, sunflower oil, high oleic sunflower oil, corn oil, palm olein oil, palm oil, safflower oil, high oleic safflower oil, MCT oil or sn2-palmitate oil, wherein the phytosterol content in ppm of the total of the specific oils within the blend is below the value obtained using the following formula (I):

$$\left[\sum_{n=1}^{13}(X_n * K_n)\right]/100 \qquad \text{Formula (I)}$$

wherein n is an integer of 1 to 13 and represents the number of the specific oils;

$X_n$ represents the percent by weight of a specific oil out of the total weight of said n specific oils;

$K_n$ represents a pre-determined threshold value of phytosterol content in ppm of a specific oil;

and wherein the pre-determined threshold value of phytosterol contents of the specific oils ($K_n$) are the following:

| Oil | $K_n$ |
|---|---|
| coconut oil | 450 |
| palm kernel oil | 900 |
| soybean oil | 1800 |
| rapeseed oil | 5800 |
| sunflower oil | 1600 |
| high oleic sunflower oil | 1500 |
| corn oil | 5900 |
| palm olein oil | 700 |
| palm oil | 530 |
| safflower oil | 8500 |
| high oleic safflower oil | 1200 |
| MCT oil | 1000 |
| sn2-palmitate oil | 300 |

It is noted that for the purpose of calculating the value obtained using the aforementioned Formula (I), the value of Xn is to be determined (provided) before blending of the specific oils. Further, in case the oil blend is being processed, Xn should be defined upon blending and prior to the process step.

It is further noted that any one or more than one of the above listed oils can be included in the blend. In addition, the blend can also comprise other, non-listed oils with reduced phytosterol content (compared to the corresponding oil of same origin). Further, the blend can also comprise other non-listed oils e.g., with no reduced phytosterol content.

In some embodiments according to the invention $X_n$ may be identical or different for each of the specified oils.

In some embodiments the phytosterol content in ppm of the total of the specific oils within the blend is less than about 90%, at times less than about 80%, at times less than about 70%, even at times less than about 60% or 50%, even at times less than about 40% or 30% and even at times less than about 20% or 10% of the value obtained using the aforementioned Formula (I).

In another one of its aspects the present invention provides an oil blend which comprises at least two oils each of which is any one of natural oil or processed oil, wherein at least one of the oils is a specific oil which is any one of coconut oil, palm kernel oil, soybean oil, rapeseed oil, sunflower oil, high oleic sunflower oil, corn oil, palm olein oil, palm oil, safflower oil, high oleic safflower oil or sn2-palmitate oil, wherein the phytosterol content in ppm of total said specific oils within the blend is below the value obtained using the following formula (II):

$$\left[\sum_{n=1}^{12}(X_n * K_n)\right]/100 \quad \text{Formula (II)}$$

wherein
n is an integer of 1 to 12 and represents the number of said specific oils;
$X_n$ represents the percent by weight of a specific oil out of the total weight of said n specific oils;
$K_n$ represents a pre-determined threshold value of phytosterol content in ppm of a specific oil;
and wherein said pre-determined threshold value of phytosterol contents of the specific oils ($K_n$) are the following:

| Oil | $K_n$ |
|---|---|
| coconut oil | 450 |
| palm kernel oil | 900 |
| soybean oil | 1800 |
| rapeseed oil | 5800 |
| sunflower oil | 1600 |
| high oleic sunflower oil | 1500 |
| corn oil | 5900 |
| palm olein oil | 700 |
| palm oil | 530 |
| safflower oil | 8500 |
| high oleic safflower oil | 1200 |
| sn2-palmitate oil | 300 |

It is noted that for the purpose of calculating the value obtained using the aforementioned Formula (II), the value of $X_n$ is to be determined (provided) before blending of the specific oils. Further, in case the oil blend is being processed, $X_n$ should be defined upon blending and prior to the process step.

It is further noted that any one or more than one of the above listed oils can be included in the blend. In addition, the blend can also comprise other, non-listed oils with reduced phytosterol content (compared to the corresponding oil of same origin). Further, the blend can also comprise other non-listed oils e.g., with no reduced phytosterol content.

In some embodiments according to the invention $X_n$ may be identical or different for each of the specified oils.

In some embodiments the phytosterol content in ppm of the total of the specific oils within the blend is less than about 90%, at times less than about 80%, at times less than about 70%, even at times less than about 60% or 50%, even at times less than about 40% or 30% and even at times less than about 20% or 10% of the value obtained using the aforementioned Formula (II).

Yet, in a further one of its aspects the present invention provides a vegetable oil blend which comprises at least two vegetable oils each of which is any one of natural vegetable oil or processed oil from vegetable source, wherein at least one of the vegetable oils is a specific vegetable oil which is any one of coconut oil, palm kernel oil, soybean oil, rapeseed oil, sunflower oil, high oleic sunflower oil, corn oil, palm olein oil, palm oil, safflower oil or high oleic safflower oil wherein the phytosterol content in ppm of total said specific oils within the blend is below the value obtained using the following formula (III):

$$\left[\sum_{n=1}^{11}(X_n * K_n)\right]/100 \quad \text{Formula (III)}$$

wherein
n is an integer of 1 to 11 and represents the number of said specific oils;
$X_n$ represents the percent by weight of a specific oil out of the total weight of said n specific oils;
$K_n$ represents a pre-determined threshold value of phytosterol content in ppm of a specific oil;
and wherein said pre-determined threshold value of phytosterol contents of the specific oils ($K_n$) are the following:

| Oil | $K_n$ |
|---|---|
| coconut oil | 450 |
| palm kernel oil | 900 |
| soybean oil | 1800 |
| rapeseed oil | 5800 |
| sunflower oil | 1600 |
| high oleic sunflower oil | 1500 |
| corn oil | 5900 |
| palm olein oil | 700 |
| palm oil | 530 |
| safflower oil | 8500 |
| high oleic safflower oil | 1200 |

It is noted that for the purpose of calculating the value obtained using the aforementioned Formula (III), the values of $X_n$ is to be determined (provided) before blending of the specific oils. Further, in case the oil blend is being processed, $X_n$ should be defined upon blending and prior to the process step.

It is further noted that any one or more than one of the above listed vegetable oils can be included in the blend. In addition, the blend can also comprise other, non-listed vegetable oils with reduced phytosterol content (compared to the corresponding oil of same origin). Further, the blend can also comprise other non-listed vegetable oils e.g., with no reduced phytosterol content.

In some embodiments according to the invention $X_n$ may be identical or different for each of the specified oils.

In some embodiments the phytosterol content in ppm of the total of the specific oils within the blend is less than about 90%, at times less than about 80%, at times less than about 70%, even at times less than about 60% or 50%, even at times less than about 40% or 30% and even at times less than about 20% or 10% of the value obtained using the aforementioned Formula (III).

In another one of its aspects the present invention provides an oil blend which comprises at least two oils each of which is any one of natural oil or processed oil, wherein at least one of the oils is any one of:

coconut oil in which the ratio phytosterol esters:free phytosterols is greater than about 0.6;

palm kernel oil in which the ratio phytosterol esters:free phytosterols is greater than about 0.6;

soybean oil in which the ratio phytosterol esters:free phytosterols is greater than about 0.5;

rapeseed oil in which the ratio phytosterol esters:free phytosterols is greater than about 1.7;

sunflower oil in which the ratio phytosterol esters:free phytosterols is greater than about 0.7;

high oleic sunflower oil in which the ratio phytosterol esters:free phytosterols is greater than about 0.7;

corn oil in which the ratio phytosterol esters:free phytosterols is greater than about 1.8;

palm olein oil in which the ratio phytosterol esters:free phytosterols is greater than about 0.4;

palm oil in which the ratio phytosterol esters:free phytosterols is greater than about 1;

safflower oil in which the ratio phytosterol esters:free phytosterols is greater than about 1.1;

high oleic safflower oil in which the ratio phytosterol esters:free phytosterols is greater than about 1.3;

MCT oil in which the ratio phytosterol esters:free phytosterols is greater than about 0.5; or sn2-palmitate oil in which the ratio phytosterol esters:free phytosterols is greater than about 0.9.

It is noted that any one or more than one of the above listed oils can be included in the blend. In addition, the blend can also comprise other, non-listed oils with reduced phytosterol content (compared to the corresponding oil of same origin). Further, the blend can also comprise other non-listed oils e.g., with no reduced phytosterol content.

In a further one of its aspects the present invention provides an oil blend which comprises at least two oils each of which is any one of natural oil or processed oil, wherein at least one of the oils is any one of:

coconut oil in which the ratio phytosterol esters:free phytosterols is greater than about 0.6;

palm kernel oil in which the ratio phytosterol esters:free phytosterols is greater than about 0.6;

soybean oil in which the ratio phytosterol esters:free phytosterols is greater than about 0.5;

rapeseed oil in which the ratio phytosterol esters:free phytosterols is greater than about 1.7;

sunflower oil in which the ratio phytosterol esters:free phytosterols is greater than about 0.7;

high oleic sunflower oil in which the ratio phytosterol esters:free phytosterols is greater than 0.7;

corn oil in which the ratio phytosterol esters:free phytosterols is greater than about 1.8;

palm olein oil in which the ratio phytosterol esters:free phytosterols is greater than about 0.4;

palm oil in which the ratio phytosterol esters:free phytosterols is greater than about 1;

safflower oil in which the ratio phytosterol esters:free phytosterols is greater than about 1.1;

high oleic safflower oil in which the ratio phytosterol esters:free phytosterols is greater than about 1.3;

sn2-palmitate oil in which the ratio phytosterol esters:free phytosterols is greater than about 0.9.

It is noted that any one or more than one of the above listed oils can be included in the blend. In addition, the blend can also comprise other, non-listed oils with reduced phytosterol content (compared to the corresponding oil of same origin). Further, the blend can also comprise other non-listed oils e.g., with no reduced phytosterol content.

In yet a further one of its aspects the present invention provides a vegetable oil blend which comprises at least two oils each of which is any one of natural vegetable oil or processed oil from vegetable source, wherein at least one of the vegetable oils is any one of:

coconut oil in which the ratio phytosterol esters:free phytosterols is greater than about 0.6;

palm kernel oil in which the ratio phytosterol esters:free phytosterols is greater than about 0.6;

soybean oil in which the ratio phytosterol esters:free phytosterols is greater than about 0.5;

rapeseed oil in which the ratio phytosterol esters:free phytosterols is greater than about 1.7;

sunflower oil in which the ratio phytosterol esters:free phytosterols is greater than about 0.7;

high oleic sunflower oil in which the ratio phytosterol esters:free phytosterols is greater than 0.7;

corn oil in which the ratio phytosterol esters:free phytosterols is greater than about 1.8;

palm olein oil in which the ratio phytosterol esters:free phytosterols is greater than about 0.4;

palm oil in which the ratio phytosterol esters:free phytosterols is greater than about 1;

safflower oil in which the ratio phytosterol esters:free phytosterols is greater than about 1.1; or high oleic safflower oil in which the ratio phytosterol esters:free phytosterols is greater than about 1.3.

It is noted that any one or more than one of the above listed vegetable oils can be included in the blend. In addition, the blend can also comprise other, non-listed vegetable oils with reduced phytosterol content (compared to the corresponding oil of same origin). Further, the blend can also comprise other non-listed vegetable oils e.g., with no reduced phytosterol content.

Yet, in a further one of its aspects the present invention provides an oil blend which comprises at least two oils, each of which is any one of natural oil or processed oil, wherein at least one of the oils is a specific oil which is any one of coconut oil, palm kernel oil, soybean oil, rapeseed oil, sunflower oil, high oleic sunflower oil, corn oil, palm olein oil, palm oil, safflower oil, high oleic safflower oil, MCT oil or sn2-palmitate oil, wherein the ratio between phytosterol esters concentration in ppm and free phytosterols concentration in ppm in total said specific oils within the blend is above the result obtained using the following formula (IV):

$$0.01 * \left[\sum_{n=1}^{13} (X_n * R_n * K_n)\right] / \left[\sum_{n=1}^{13} (K_n)\right] \quad \text{Formula (IV)}$$

wherein
n is an integer of 1 to 13 and represents the number of said specific oils;

$X_n$ represents the percent by weight of a specific oil out of the total weight of said n oils;

$R_n$ represents a pre-determined threshold value of the ratio between the phytosterol esters concentration (in ppm) and the free phytosterol concentration (in ppm) in the specific oil;

$K_n$ represents a pre-determined threshold value of phytosterol content in ppm of said specific oil;

and wherein the pre-determined threshold value of the ratio between phytosterol esters concentration in ppm and free phytosterols concentration in ppm in the specific oils ($R_n$) are the following:

| Oil | $R_n$ |
| --- | --- |
| coconut oil | 0.6 |
| palm kernel oil | 0.6 |
| soybean oil | 0.5 |
| rapeseed oil | 1.7 |
| sunflower oil | 0.7 |
| high oleic sunflower oil | 0.7 |
| corn oil | 1.8 |
| palm olein oil | 0.4 |
| palm oil | 1 |
| safflower oil | 1.1 |
| high oleic safflower oil | 1.3 |
| MCT oil | 0.5 |
| sn2-palmitate oil | 0.9 | and wherein said pre-determined threshold value of phytosterol contents of the specific oils ($K_n$) are the following:

| Oil | $K_n$ |
| --- | --- |
| coconut oil | 450 |
| palm kernel oil | 900 |
| soybean oil | 1800 |
| rapeseed oil | 5800 |
| sunflower oil | 1600 |
| high oleic sunflower oil | 1500 |
| corn oil | 5900 |
| palm olein oil | 700 |
| palm oil | 530 |
| safflower oil | 8500 |
| high oleic safflower oil | 1200 |
| MCT oil | 1000 |
| sn2-palmitate oil | 300 |

In some embodiments (e.g., as detailed herein below) the ratio between phytosterol esters concentration in ppm and free phytosterols concentration in ppm in the specific oils are above the values designated herein above.

In some embodiments the ratio between phytosterol esters concentration in ppm and free phytosterols concentration in ppm in total said specific oils within the blend is about 10% or 20%, at times about 40% or 60%, at times about 80% or 100%, even at times about 120% or 150% and even at times about 200% or 300% above the result obtained using the aforementioned formula (IV).

It is noted that for the purpose of calculating the value obtained using the aforementioned Formula (IV), the value of $X_n$ is to be determined (provided) before blending of the specific oils. Further, in case the oil blend is being processed, $X_n$ should be defined upon blending and prior to the process step.

It is further noted that any one or more than one of the above listed oils can be included in the blend. In addition, the blend can also comprise other, non-listed oils with reduced phytosterol content (compared to the corresponding oil of same origin). Further, the blend can also comprise other non-listed oils e.g., with no reduced phytosterol content.

In some embodiments according to the invention $X_n$ may be identical or different for each of the specified oils.

In another one of its aspects the present invention provides an oil blend which comprises at least two oils, each of which is any one of natural oil or processed oil, wherein at least one of the oils is a specific oil which is any one of coconut oil, palm kernel oil, soybean oil, rapeseed oil, sunflower oil, high oleic sunflower oil, corn oil, palm olein oil, palm oil, safflower oil, high oleic safflower oil or sn2-palmitate oil, wherein the ratio between phytosterol esters concentration in ppm and free phytosterols concentration in ppm in total said specific oils within the blend is above the result obtained using the following formula (V):

$$0.01 * \left[\sum_{n=1}^{12} (X_n * R_n * K_n)\right] / \left[\sum_{n=1}^{12} (K_n)\right] \quad \text{Formula (V)}$$

wherein n is an integer of 1 to 12 and represents the number of said specific oils;

$X_n$ represents the percent by weight of a specific oil out of the total weight of said n specific oils;

$R_n$ represents a pre-determined threshold value of the ratio between the phytosterol esters concentration (in ppm) and the free phytosterol concentration (in ppm) in the specific oil;

$K_n$ represents a pre-determined threshold value of phytosterol content in ppm of said specific oil;

and wherein the pre-determined threshold value of the ratio between phytosterol esters concentration in ppm and free phytosterols concentration in ppm in the specific oils ($R_n$) are the following:

| Oil | $R_n$ |
| --- | --- |
| coconut oil | 0.6 |
| palm kernel oil | 0.6 |
| soybean oil | 0.5 |
| rapeseed oil | 1.7 |
| sunflower oil | 0.7 |
| high oleic sunflower oil | 0.7 |
| corn oil | 1.8 |
| palm olein oil | 0.4 |
| palm oil | 1 |
| safflower oil | 1.1 |
| high oleic safflower oil | 1.3 |
| sn2-palmitate oil | 0.9 | and wherein said pre-determined threshold value of phytosterol contents of the specific oils ($K_n$) are the following:

| Oil | $K_n$ |
| --- | --- |
| coconut oil | 450 |
| palm kernel oil | 900 |
| soybean oil | 1800 |
| rapeseed oil | 5800 |
| sunflower oil | 1600 |
| high oleic sunflower oil | 1500 |
| corn oil | 5900 |
| palm olein oil | 700 |
| palm oil | 530 |
| safflower oil | 8500 |
| high oleic safflower oil | 1200 |
| sn2-palmitate oil | 300 |

In some embodiments, e.g., as detailed herein below, the ratio between phytosterol esters concentration in ppm and free phytosterols concentration in ppm in the specific oils are above the values designated herein above.

In some embodiments the ratio between phytosterol esters concentration in ppm and free phytosterols concentration in ppm in total said specific oils within the blend is about 10% or 20%, at times about 40% or 60%, at times about 80% or 100%, even at times about 120% or 150% and even at times about 200% or 300% above the result obtained using the aforementioned formula (V).

It is noted that for the purpose of calculating the value obtained using the aforementioned Formula (V), the value of $X_n$ is to be determined (provided) before blending of the specific oils. Further, in case the oil blend is being processed, $X_n$ should be defined upon blending and prior to the process step.

In some embodiments according to the invention $X_n$ may be identical or different for each of the specified oils.

It is further noted that any one or more than one of the above listed oils can be included in the blend. In addition, the blend can also comprise other, non-listed oils with reduced phytosterol content (compared to the corresponding oil of same origin). Further, the blend can also comprise other non-listed oils e.g., with no reduced phytosterol content.

Yet, in a further one of its aspects the present invention provides a vegetable oil blend which comprises at least two vegetable oils, each of which is any one of natural vegetable oil or processed oil from vegetable source, wherein at least one of the vegetable oils is a specific oil which is any one of coconut oil, palm kernel oil, soybean oil, rapeseed oil, sunflower oil, high oleic sunflower oil, corn oil, palm olein oil, palm oil, safflower oil or high oleic safflower oil, wherein the ratio between phytosterol esters concentration in ppm and free phytosterols concentration in ppm in total said specific oils within the blend is above the result obtained using the following formula (VI):

$$0.01 * \left[\sum_{n=1}^{11} (X_n * R_n * K_n)\right] / \left[\sum_{n=1}^{11} (K_n)\right] \quad \text{Formula (VI)}$$

wherein n is an integer of 1 to 11 and represents the number of said specific oils;

$X_n$ represents the percent by weight of a specific oil out of the total weight of said n oils;

$R_n$ represents a pre-determined threshold value of the ratio between the phytosterol esters concentration (in ppm) and the free phytosterol concentration (in ppm) in the specific oil;

$K_n$ represents a pre-determined threshold value of phytosterol content in ppm of said specific oil;

and wherein the pre-determined threshold value of the ratio between phytosterol esters concentration in ppm and free phytosterols concentration in ppm in the specific oils ($R_n$) are the following:

| Oil | $R_n$ |
|---|---|
| coconut oil | 0.6 |
| palm kernel oil | 0.6 |
| soybean oil | 0.5 |
| rapeseed oil | 1.7 |
| sunflower oil | 0.7 |
| high oleic sunflower oil | 0.7 |
| corn oil | 1.8 |
| palm olein oil | 0.4 |
| palm oil | 1 |
| safflower oil | 1.1 |
| high oleic safflower oil | 1.3 | and wherein said pre-determined threshold value of phytosterol contents of the specific oils ($K_n$) are the following:

| Oil | $K_n$ |
|---|---|
| coconut oil | 450 |
| palm kernel oil | 900 |
| soybean oil | 1800 |
| rapeseed oil | 5800 |
| sunflower oil | 1600 |
| high oleic sunflower oil | 1500 |
| corn oil | 5900 |
| palm olein oil | 700 |
| palm oil | 530 |
| safflower oil | 8500 |
| high oleic safflower oil | 1200 |

In some embodiments, e.g., as detailed herein below, the ratio between phytosterol esters concentration in ppm and free phytosterols concentration in ppm in the specific oils are above the values designated herein above.

In some embodiments the ratio between phytosterol esters concentration in ppm and free phytosterols concentration in ppm in total said specific oils within the blend is about 10% or 20%, at times about 40% or 60%, at times about 80% or 100%, even at times about 120% or 150% and even at times about 200% or 300% above the result obtained using the aforementioned formula (VI).

It is noted that for the purpose of calculating the value obtained using the aforementioned Formula (VI), the value of $X_n$ is to be determined (provided) before blending of the specific oils. Further, in case the oil blend is being processed, $X_n$ should be defined upon blending and prior to the process step.

In some embodiments according to the invention $X_n$ may be identical or different for each of the specified oils.

It is further noted that any one or more than one of the above listed vegetable oils can be included in the blend. In addition, the blend can also comprise other, non-listed vegetable oils with reduced phytosterol content (compared to the corresponding oil of same origin). Further, the blend can also comprise other non-listed vegetable oils e.g., with no reduced phytosterol content.

In some embodiments the oil blends according to the invention may comprise at least three oils, at least four oils, at least five oils, at least six oils, at least seven oils, at least eight oils, at least nine oils, at least ten oils, at least eleven oils, at least twelve oils, at least thirteen oils, at least fourteen oils etc. The oils may be vegetable oils, natural oils, processed oils from vegetable source or processed oils as herein defined.

In some embodiments the oil blends according to the invention may comprise or contain at least two, at times at least three, at times at least four and even at times at least five of the following oils: coconut oil, palm kernel oil, soybean oil, rapeseed oil, sunflower oil, high oleic sunflower oil, corn oil, palm olein oil, palm oil, safflower oil, high oleic safflower oil, MCT oil or sn2-palmitate oil.

In some embodiments the vegetable oil blends according to the invention comprises or contains at least two, at times at least three, at times at least four and even at times, at least five of the following oils: coconut oil, palm kernel oil, soybean oil, rapeseed oil, sunflower oil, high oleic sunflower oil, corn oil, palm olein oil, palm oil, safflower oil or high oleic safflower oil.

In some embodiments the oil blends according to the invention may comprise 1, 2, 3, 4, 5, 6, 7, 8, 9, 10, 11, 12 or 13 specific oils. Thus, in some embodiments "n" may be an integer of 1 to 2, 1 to 3, 1 to 4, 1 to 5, 1 to 6, 1 to 7, 1 to 8, 1 to 9, 1 to 10, 1 to 11, 1 to 12 or 1 to 13. In a specific embodiment "n" is an integer of 1 to 13. In a further specific embodiment "n" is an integer of 1 to 12. In a further specific embodiment "n" is an integer of 1 to 11.

In some embodiments the vegetable oil blends according to the invention may comprise 1, 2, 3, 4, 5, 6, 7, 8, 9, 10, 11 or 12 specific oils. Thus, in some embodiments "n" may be an integer of 1 to 2, 1 to 3, 1 to 4, 1 to 5, 1 to 6, 1 to 7, 1 to 8, 1 to 9, 1 to 10, 1 to 11 or 1 to 12. In a specific embodiment "n" is an integer of 1 to 12.

In some embodiments "n" is an integer of 1 to 2. In some embodiments "n" is an integer of 1 to 3. In some embodiments "n" is an integer of 1 to 4. In some embodiments "n" is an integer of 1 to 5. In some embodiments "n" is an integer of 1 to 6. In some embodiments "n" is an integer of 1 to 7. In some embodiments "n" is an integer of 1 to 8. In some embodiments "n" is an integer of 1 to 9. In some embodiments "n" is an integer of 1 to 10. In some embodiments "n" is an integer of 1 to 11. In some embodiments "n" is an integer of 1 to 12. In some embodiments "n" is an integer of 1 to 13.

In some embodiments the oil blends according to the invention may comprise or contain one of the following oil combinations: coconut oil, soybean oil, high oleic sunflower oil and palm oil; or, coconut oil, soybean oil and high oleic safflower oil; or, palm kernel oil, rapeseed oil, sunflower oil, high oleic sunflower oil and palm oil; or, palm kernel oil, rapeseed oil and sunflower oil; or, palm kernel oil, soybean oil, rapeseed oil, sunflower oil and palm oil; coconut oil, soybean oil and palm oil; or, palm kernel oil, soybean oil, rapeseed oil and sunflower oil; or, palm kernel oil, soybean oil, rapeseed oil, sunflower oil and high oleic sunflower oil; or, coconut oil, rapeseed oil, sunflower oil and high oleic sunflower oil; or, palm kernel oil, rapeseed oil, sunflower oil or, high oleic sunflower oil; coconut oil, rapeseed oil and sunflower oil.

In some embodiments the oil blends according to the invention comprise OPO (sn2-palmitate), palm kernel oil, rapeseed oil and sunflower oil with less than about 2000 ppm phytosterols, at times less than about 1500 ppm, at times less than about 1000 ppm, at times less than about 700 ppm, at times less than about 600, at times less than about 500 ppm, at times less than about 400 ppm, even at times less than about 200 ppm. In some embodiments the OPO percentage (w/w) out of the total oils is 1%-90%, at times 5%-70%, at times 10%-60, at times 20%-50%, even at times 30%-40%; the palm kernel oil percentage (w/w) out of the total oils is 1%-90%, at times 5%-70%, at times 7%-50%, at times 10%-40%, at times 15%-30%, even at times 20%-25%; the rapeseed oil percentage (w/w) out of the total oils is 1%-90%, at times 5%-70%, at times 7%-50%, at times 10%-40%, even at times, 15%-30%; the sunflower oil percentage (w/w) out of the total oils is 1%-90%, at times 3%-70%, at times 5%-40, even at times, 10%-20%.

In some embodiments the oil blends according to the invention comprise coconut oil, soybean oil, high oleic sunflower oil and palm oil with less than about 2000 ppm phytosterols, at times less than about 1500 ppm, at times less than about 1000 ppm, at times less than about 700 ppm, at times less than about 600 ppm, at times less than about 500 ppm, at times less than about 400 ppm, at times less than about 200 ppm. In some embodiments the coconut oil percentage (w/w) out of the total oils is 1%-90%, at times 5%-70%, at times 7%-50%, at times 10%-40%, at times 15%-30%, even at times, 20%-25%; the soybean oil percentage (w/w) out of the total oils is 1%-90%, at times 5%-70%, at times 7%-50%, at times 10%-40%, at times 15%-30%, even at times, 20%-25%; the high oleic sunflower oil percentage (w/w) out of the total oils is 1%-90%, at times 3%-70%, at times 5%-40, even at times, 10%-20%; the palm oil percentage (w/w) out of the total oils is 1%-90%, at times 10%-70%, at times 20%-60%, at times 30%-50%, even at times, 40%-45%.

In some embodiments the oil blends according to the invention comprise coconut oil, soybean oil and high oleic safflower oil with less than about 2000 ppm phytosterols, at times less than about 1500 ppm, at times less than about 1000 ppm, at times less than about 700 ppm, at times less than about 600, at times less than about 500 ppm, at times less than about 400 ppm, even at times less than about 200 ppm. In some embodiments the coconut oil percentage (w/w) out of the total oils is 1%-90%, at times 5%-70%, at times 10%-50%, at times 20%-40%, even at times 25%-35%; the soybean oil percentage (w/w) out of the total oils is 1%-90%, at times 5%-70%, at times 10%-50%, at times 20%-40%, even at times 25%-35%; the high oleic safflower oil percentage (w/w) out of the total oils is 1%-90%, at times 5%-70%, at times 10%-60%, at times 20%-50%, even at times, 30%-45%.

In some embodiments the oil blends according to the invention comprise palm kernel oil, soybean oil, high oleic sunflower oil and palm oil with less than about 2000 ppm phytosterols, at times less than about 1500 ppm, at times less than about 1000 ppm, at times less than about 700 ppm, at times less than about 600, at times less than about 500 ppm, at times less than about 400 ppm, even at times, less than about 200 ppm. In some embodiments the palm kernel oil percentage (w/w) out of the total oils is 1%-90%, at times 5%-70%, at times 10%-50%, even at times, 20%-30%; the soybean oil percentage (w/w) out of the total oils is 1%-90%, at times 3%-50%, even at times 10%-20%; the high oleic sunflower oil percentage (w/w) out of the total oils is 1%-90%, at times 3%-50%, even at times, 10%-20%; the palm oil percentage (w/w) out of the total oils is 1%-90%, at times 5%-70%, at times 10%-60%, at times 20%-50%, even at times, 30%-45%.

FIG. 1 illustrates a non-limiting embodiment of the invention in which specific oil (100), designated as (A) in the figure, is subjected to means (102) to reduce the phytosterol content thereof resulting with oil (104) with reduced phytosterol content, designated as (A') in the figure. Oil (104) is then mixed (108) with another oil (106) designated as (B) in the figure (which may have a reduced phytosterol content) to produce an oil blend with reduced phytosterol content (110) (designated in the figure as A'+B). The oil blend with the reduced phytosterol content (110) may optionally be further blended (114) with at least one further oil (112), designated in the figure as oil (C) (which may have a reduced phytosterol content), resulting with an oil blend with reduced phytosterol content (116) (designated in the figure as A'+B+C). It is noted that for the purpose of calculating the values obtained using the various formulae disclosed herein [formulae (I) to (VI)] the value of $X_n$ is to be determined (provided) before blending of the oils.

Figure 2:
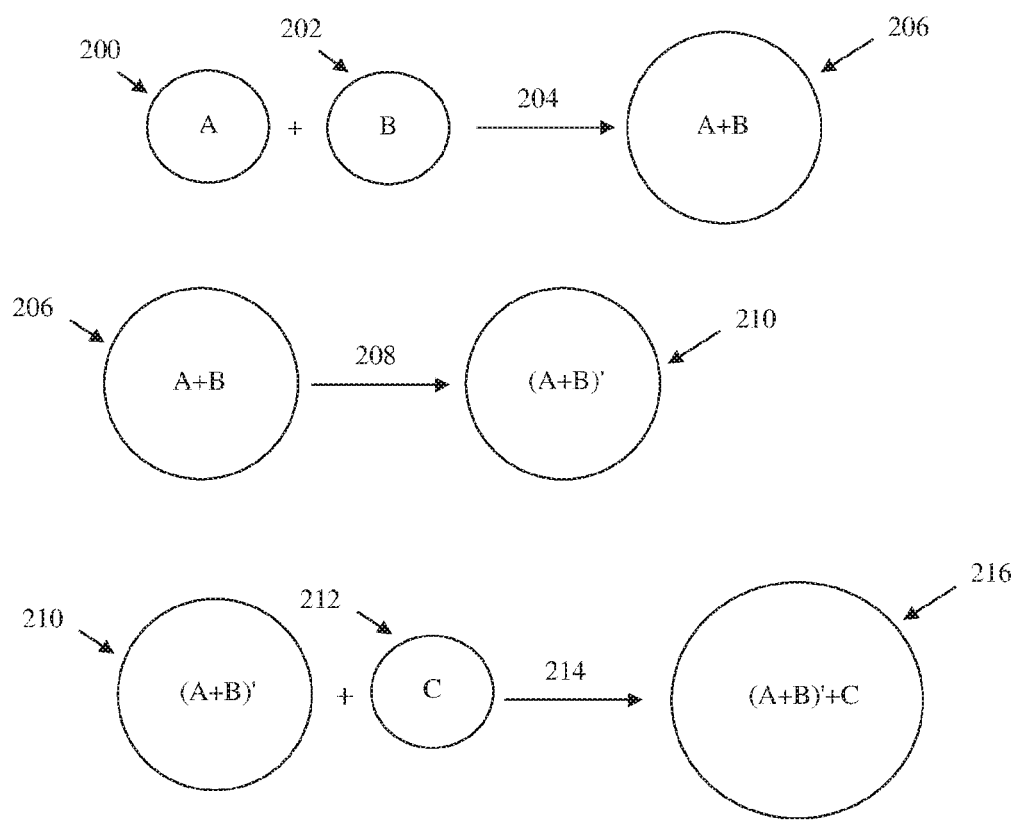
FIG. 2 illustrates an embodiment of the invention according to which one specific oil is mixed with another specific oil, followed by reduction of the phytosterol content of the resulted blend.

FIG. 2 illustrates a non-limiting embodiment of the invention in which specific oil (200), designated as (A) in the figure, is mixed (204) with another specific oil (202), designated as (B) in the figure. The resulted oil blend (206) (designated as A+B in the figure) is subjected to means (208) to reduce the phytosterol content thereof resulting with an oil blend (210), designated as (A+B)' in the figure, with reduced phytosterol content. The oil blend with the reduced phytosterol content (210) may optionally be further blended (214) with at least one further oil (212), designated in the figure as oil (C) (which may have a reduced phytosterol content) resulting with an oil blend (216) with reduced phytosterol content, designated as (A+B)'+C in the figure. It is noted that for the purpose of calculating the values obtained using the various formulae disclosed herein [formulae (I) to (VI)], the value of $X_n$ is to be determined (provided) before blending of the oils.

In some embodiments the oil blend according to the invention may further comprise at least one structured triglyceride, preferably enriched with palmitic acid at the sn-2 position of the triglyceride.

In some embodiments the vegetable oil blend according to the invention may further comprise at least one of MCT oil and sn2-palmitate oil.

In another one of its aspects the present invention provides an oil blend which consists at least one vegetable oil and at least one of MCT oil and sn2-palmitate oil wherein in the blend the total amount of phytosterols is less than about 4000 ppm.

In another one of its aspects the present invention provides an oil blend which contains a total amount of phytosterols of less than about 4000 ppm.

In another one of its aspects the present invention provides a vegetable oil blend which contains a total amount of phytosterols of less than about 4000 ppm.

In some embodiments the oil blend according to the invention contains a total amount of phytosterols of less than about 4000 ppm.

In some embodiments the vegetable oil blend according to the invention contains a total amount of phytosterols of less than about 4000 ppm.

In some embodiments the oil blends according to the invention contain total amount of phytosterols of less than about 3000 or 2000 ppm, at times less than about 1500 or 1000 ppm, even at times less than about 800 or 600 ppm, even at times less than about 400 or 300 ppm and even at times less than about 200 or 100 ppm.

In some embodiments the vegetable oil blends according to the invention contain total amount of phytosterols of less than about 3000 or 2000 ppm, at times less than about 1500 or 1000 ppm, even at times less than about 800 or 600 ppm, even at times less than about 400 or 300 ppm and even at times less than about 200 or 100 ppm.

The following is accepted nomenclature of several saturated fatty acids: caprylic acid (octanoic acid, C8:0), capric acid (decanoic acid, C10:0), lauric acid (dodecanoic acid, C12:0), myristic acid (tetradecanoic acid, C14:0), palmitic acid (hexadecanoic acid, C16:0), stearic acid (octadecanoic acid, C18:0).

The following is accepted nomenclature of several unsaturated fatty acid: oleic acid (C18:1), linoleic acid (C18:2), α-linolenic acid (C18:3), arachidonic acid (C20:4), eicosapentaenoic acid (EPA) (C20:5), docosapentaenoic acid (DPA) (C22:5) and docosahexaenoic acid (DHA) (C22:6).

In some embodiments the fatty acid composition of the oil blend according to the invention is as follows:
  0-10% C8:0 fatty acids out of the total fatty acids;
  0-10% C10:0 fatty acids out of the total fatty acids;
  0-22% C12:0 fatty acids out of the total fatty acids;
  0-15% C14:0 fatty acids out of the total fatty acids;
  5-55% C16:0 fatty acids out of the total fatty acids;
  1-7% C18:0 fatty acids out of the total fatty acids;
  20-75% C18:1 fatty acids out of the total fatty acids;
  2-40% C18:2 fatty acids out of the total fatty acids;
  0-8% C18:3 fatty acids out of the total fatty acids; and
  other fatty acids present in levels of less than 8% of the total fatty acids.

In some embodiments, the oil blends according to the invention have an endogenic tocopherol (TCP) concentration below about 800 ppm.

Thus, in a further one of its aspects the present invention provides oil blends as herein disclosed wherein the oil blends have an endogenic tocopherol concentration below about 800 ppm.

In some embodiments the oil blends (e.g., vegetable oil blends) according to the invention have endogenic tocopherol concentration below about 600 ppm, at times below about 500 ppm or 400 ppm, at times below about 300 ppm, even at times below about 200 ppm, even at times, below about 100 ppm, at times below about 50 ppm, at times below about 30 ppm, at times below about 20 ppm, even at times below about 10 ppm.

In some embodiments the ratio (w/w) between alpha tocopherols levels to non-alpha tocopherols levels in the oil blends (e.g., vegetable oil blends) according to the invention is at least about 5. At times said ratio is about 8 or above, at times about 10 or above, at times about 15 or above, at times about 20 or above, even at times about 10 to about 20.

In some embodiments the percentage of diacylglycerol level (w/w) out of the oil blends (e.g., vegetable oil blends) according to the invention is at most about 0.5%. At times said percentage is about 0.3% or below, at times about 0.2% or below, at times about 0.1% or below, at times about 0.05% or below, even at times about 0.01% or below.

In another one of its aspects the present invention provides an infant formula, parenteral formula, baby food, toddler formula, child formula or adult formula comprising any one of the oil blends and/or vegetable oil blends according to the present invention.

In some embodiments the w/w ratio between cholesterol, present in a formula (e.g., infant formula) of the invention, to phytosterol is at least about 1.

In some embodiments a formula of the invention comprises at least about 5 mg cholesterol/100 g formula, at times at least about 10 mg cholesterol/100 g formula, at times at least about 20 mg cholesterol/100 g formula, at times at least about 30 mg cholesterol/100 g formula, at times about 40 mg cholesterol/100 g formula or above, at times about 60 mg cholesterol/100 g formula or above, at times about 80 mg cholesterol/100 g formula or above, at times about 100 mg cholesterol/100 g formula or above, at times between about 30 mg to about 200 mg cholesterol/100 g formula, at times between about 50 mg to about 150 mg cholesterol/100 g formula and at times between about 60 mg to about 130 mg cholesterol/100 g formula.

In some embodiments the ratio (w/w) between alpha tocopherols levels to non-alpha tocopherols levels in a formula of the invention is at least about 5. At times said ratio is about 8 or above, at times about 10 or above, at times about 15 or above, at times about 20 or above and at times about 10 to about 20.

In some embodiments the percentage of diacylglycerol levels (w/w) out of the oil blend (e.g., vegetable oil blend) of the invention in a formula (e.g., an infant formula) according to the invention is at most 0.5%. At times said percentage is about 0.3% or below, at times about 0.2% or below, at times about 0.1% or below, at times about 0.05% or below and at times about 0.01% or below.

As used herein the term "w/w" refers to a weight per weight ratio.

In some embodiments the w/w ratio between cholesterol, present in a formula of the invention, to phytosterol is at least about 1, at times at least about 1.5, at times at least about 2, at times at least about 5, even at times at least about 10. It is noted that the cholesterol may be originated from the formula (e.g., infant formula, toddler formula, child formula or adult formula, each of which may be parenteral formula) for example as an added supplement or originated from sources comprised within the formula.

In some embodiments according to the invention the coconut oil contains less than about 550 or 450 ppm phytosterols, at times less than about 400 or 350 phytosterols, even at times less than about 300 or 250 ppm phytosterols, even at times less than about 200 or 150 ppm phytosterols, even at times less than about 100 ppm phytosterols.

In some embodiments according to the invention the palm kernel oil contains less than about 1000 or 850, at times less than about 750 or 700 ppm phytosterols, at times less than about 650 or 550 ppm phytosterols, at times less than about 500 or 450 ppm phytosterols, even at times less than about 400 or 350 ppm phytosterols and even at times less than about 300 or 250 ppm phytosterols.

In some embodiments according to the invention the soybean oil contains less than about 1700 or 1500 ppm phytosterols, at times less than about 1300 or 1000 ppm phytosterols, at times less than about 800 or 600 ppm phytosterols, even at times less than about 500 or 400 ppm phytosterols, even at times less than about 300 or 200 ppm phytosterols.

In some embodiments according to the invention the rapeseed oil contains less than about 8000 or 7000, at times, less than about 5500 or 4500 ppm phytosterols, at times less than about 4000 or 3500 ppm phytosterols, at times less than about 3000 or 2500 ppm phytosterols, even at times less than about 2000 or 1500 ppm phytosterols, even at times less than about 1000, 800 or 500 ppm phytosterols.

In some embodiments according to the invention the sunflower oil contains less than about 2000 or 1500 ppm phytosterols, at times less than about 1200 or 1000 ppm phytosterols, at times less than about 800 or 600 ppm phytosterols, even at times less than about 500 or 400 ppm phytosterols, even at times less than about 300 or 200 ppm phytosterols.

In some embodiments according to the invention the high oleic sunflower oil contains less than about 2000 or 1700 ppm phytosterols, at times less than about 1500 or 1300 ppm phytosterols, at times less than about 1000 or 800 ppm phytosterols, even at times less than about 700 or 600 ppm phytosterols, even at times less than about 500 or 400 ppm phytosterols.

In some embodiments according to the invention the corn oil contains less than about 5000 or 4500 ppm phytosterols, at times less than about 4000 or 3500 ppm phytosterols, at times less than about 3000 or 2500 ppm phytosterols, even at times less than about 2000 or 1500 ppm phytosterols, even at times less than about 1000 or 500 ppm phytosterols.

In some embodiments according to the invention the palm olein oil contains less than about 600 or 500 ppm phytosterols, at times less than about 450 or 400 ppm phytosterols, at times less than about 350 or 300 ppm phytosterols, even at times less than about 270, 250 or 200 ppm phytosterols, even at times less than about 150 or 100 ppm phytosterols.

In some embodiments according to the invention the palm oil contains less than about 500 or 450 ppm phytosterols, at times less than about 400 or 350 ppm phytosterols, at times less than about 300 or 250 ppm phytosterols, even at times less than about 200 or 150 ppm phytosterols, even at times less than about 100 or 50 ppm phytosterols.

In some embodiments according to the invention the safflower oil contains less than about 8000 or 7000 ppm phytosterols, at times less than about 6000 or 5000 ppm phytosterols, at times less than about 4000 or 3000 ppm phytosterols, even at times less than about 2000, 1900 or 1500 ppm phytosterols, even at times less than about 1000, 500, 300 or 150 ppm phytosterols.

In some embodiments according to the invention the high oleic safflower oil contains less than about 2500 or 2000 ppm phytosterols, at times less than about 1500 or 1000 ppm phytosterols, at times less than about 800 or 600 ppm phytosterols, even at times less than about 500 or 400 ppm phytosterols, even at times less than about 300 or 200 ppm phytosterols.

In some embodiments according to the invention the MCT oil contains less than about 900 or 800 ppm phytosterols, at times less than about 700 or 600 ppm phytosterols, at times less than about 500 or 400 ppm phytosterols, even at times less than about 300 or 200 ppm phytosterols, even at times less than about 100 or 50 or 10 ppm phytosterols.

In some embodiments according to the invention the sn2-palmitate oil contains less than about 250 ppm phytosterols, at times less than about 200 ppm phytosterols, at times less than about 150 ppm phytosterols, even at times less than about 100 ppm phytosterols, even at times less than about 50 or 10 ppm phytosterols.

In some embodiments according to the invention the phytosterol esters to free phytosterols ratio in said coconut oil is greater than about 0.8, at times greater than about 1 or 1.5, at times greater than about 2 or 3, at times greater than about 5, even at times greater than about 10.

In some embodiments according to the invention the phytosterol esters to free phytosterols ratio in said palm kernel oil is greater than about 0.8 or 1, at times greater than about 1.5 or 2, at times greater than about 3 or 4, at times greater than about 5, even at times greater than about 10.

In some embodiments according to the invention the phytosterol esters to free phytosterols ratio in said soybean oil is greater than about 0.6 or 1, at times greater than about 1.5 or 2, at times greater than about 3 or 4, at times greater than about 5, even at times greater than about 10.

In some embodiments according to the invention the phytosterol esters to free phytosterols ratio in said rapeseed oil is greater than about 1.7 or 2, at times greater than about 2.5, 3, 3.5 or 4, at times greater than about 5, 6 or 10, at times greater than about 13 or 15, even at times greater than about 20.

In some embodiments according to the invention the phytosterol esters to free phytosterols ratio in said sunflower oil is greater than about 0.8 or 1, at times greater than about 1.5 or 2, at times greater than about 3 or 4, at times greater than about 5 or 10, even at times greater than about 15.

In some embodiments according to the invention the phytosterol esters to free phytosterols ratio in said high oleic sunflower oil is greater than about 0.8 or 1, at times greater than about 1.5 or 2, at times greater than about 3 or 3.5, at times greater than about 4 or 6, even at times greater than about 10.

In some embodiments according to the invention the phytosterol esters to free phytosterols ratio in said corn oil is greater than about 2 or 2.5, at times greater than about 3 or 4, at times greater than about 6 or 8, at times greater than about 10, even at times greater than about 15.

In some embodiments according to the invention the phytosterol esters to free phytosterols ratio in said palm olein oil is greater than about 0.5 or 0.8, at times greater than about 1 or 1.5, at times greater than about 2 or 3, at times greater than about 5, even at times greater than about 10.

In some embodiments according to the invention the phytosterol esters to free phytosterols ratio in said palm oil is greater than about 1.2 or 1.5, at times greater than about 2 or 2.5, at times greater than about 3 or 4, at times greater than about 6, even at times greater than about 10.

In some embodiments according to the invention the phytosterol esters to free phytosterols ratio in said safflower oil is greater than about 1.3 or 1.5, at times greater than about 2 or 2.5, at times greater than about 3 or 4, at times greater than about 6, even at times greater than about 10.

In some embodiments according to the invention the phytosterol esters to free phytosterols ratio in said high oleic safflower oil is greater than about 1.5 or 2, at times greater than about 3 or 4, at times greater than about 6 or 8, at times greater than about 10, even at times greater than about 15.

In some embodiments according to the invention the phytosterol esters to free phytosterols ratio in said MCT oil is greater than about 0.6 or 0.8, at times greater than about 1 or 1.5, at times greater than about 2 or 2.5, at times greater than about 3 or 4, even at times greater than about 5.

In some embodiments according to the invention the phytosterol esters to free phytosterols ratio in said sn2-palmitate oil is greater than about 1.1 or 1.5, at times greater than about 2 or 2.5, at times greater than about 3 or 4, at times greater than about 5, even at times greater than about 10.

The oil blends (e.g., vegetable oil blends) according to the present invention may be comprised within nutritional compositions, pharmaceutical compositions, nutraceutical compositions, parenteral nutrition compositions, functional foods or medical foods.

The oil blends (e.g., vegetable oil blends) according to the present invention may be comprised within an infant formula, at times within a parenteral formula, at times within baby food, at times within toddler formula, at times within a child formula, even at times within an adult formula.

In another one of its aspects the present invention provides a process for the preparation of the oil blends (e.g., a vegetable oil blend) according to the invention, the process comprises providing one or more means for reducing the phytosterol content of at least one oil and mixing the resulted oil with reduced phytosterol content with at least one other oil to thereby obtain an oil blend with reduced phytosterol content. The process may optionally further comprise addition of at least one further oil to the resulted oil blend.

In a further one of its aspects the present invention provides a process for the preparation of the oil blends (e.g., a vegetable oil blend) according to the invention, the process comprises mixing at least two oils, providing one or more means for reducing the phytosterol content of the resulted mixture of the at least two oils to thereby obtain an oil blend with reduced phytosterol content. The process may optionally further comprise addition of at least one further oil to the resulted oil blend.

In a further one of its aspects the present invention provides a process for the preparation of the oil blends (e.g., a vegetable oil blend) according to the invention, the process comprises providing one or more means for reducing the phytosterol content of at least one oil and mixing the same with at least one other oil which underwent a process for phytosterol reduction (e.g., subjected to one or more means for reducing the phytosterol content thereof), to thereby obtain an oil blend with reduced phytosterol content. The process may optionally further comprise addition of at least one further oil to the resulted oil blend.

In some embodiments the phytosterol content of the least one oil or the phytosterol content of the oil blend is reduced by means of column chromatography, distillation, molecular distillation, absorption on oil insoluble matrix, fractionation, solvent extraction or any combination of the same.

In some embodiments according to the process according to the invention, the phytosterol content of one or more oils (alone or blended) is reduced by molecular distillation.

In some embodiments according to the process according to the invention, the means for reducing the phytosterol content of one or more oils (alone or blended) comprise molecular distillation.

In some embodiments the oil blend according to the invention may be obtained by means of evaporation e.g., by transferring an oil (one oil or a mixture of at least two oils) through a molecular distillation unit (referred to herein also as a short path) under conditions such as vacuum (which may be high vacuum) and temperature allowing removal or reducing (to a certain degree) the phytosterol content of the oil.

In some embodiments according to the process of the invention the phytosterol content of one oil or a mixture of at least two oils may be reduced by subjecting the oil to evaporation means e.g., by transferring the oil through molecular distillation unit under conditions such as vacuum (e.g., high vacuum) and temperature allowing removal or reducing (to a certain degree) the phytosterol content of the oil.

In another one of its aspects the present invention provides a process for reducing phytosterol content in an oil (e.g., vegetable oil), the process comprising subjecting the oil to molecular distillation in a distillation system, wherein the molecular distillation is performed under specific temperature and vacuum conditions, and wherein the weight percentage of the oil distillate resulting from the molecular distillation is between about 2% to about 60% out of the total weight of the oil subjected to said molecular distillation.

In yet a further one of its aspects the present invention provides a process for reducing phytosterol content in an oil (e.g., vegetable oil), the process comprises subjecting the oil to molecular distillation in a distillation system, wherein the system comprises vacuum generating means and at least one condenser, wherein the temperature of the oil under distillation is between about 50° C. to about 400° C. and the vacuum is between about 0.0001 mbar to about 3 mbar, the vacuum being measured at a location in the system between vacuum producing means and a condenser and wherein the weight percentage of the oil distillate resulting from the molecular distillation is between about 2% to about 60% out of the total weight of the oil subjected to the molecular distillation.

In a further one of its aspects the present invention provides a process for the preparation of an oil blend which comprises at least two oils wherein at least one of the oils has reduced phytosterol content, the process comprising:

subjecting at least one oil to molecular distillation in a distillation system, wherein the molecular distillation is performed under specific temperature and vacuum conditions, and wherein the weight percentage of the at least one oil distillate resulting from the molecular distillation is between about 2% to about 60% out of the total weight of the at least one oil subjected to the molecular distillation; and blending the at least one distilled oil with at least one other oil, wherein the at least one other oil is optionally also subjected to the molecular distillation;

to thereby obtain an oil blend with reduced phytosterol content.

In yet a further one of its aspects the present invention provides a process for the preparation of an oil blend which comprises at least two oils wherein at least one of the oils has reduced phytosterol content, the process comprising:

subjecting at least one oil to molecular distillation in a distillation system, wherein the system comprises vacuum generating means and at least one condenser, wherein the temperature of the at least one oil under distillation is between about 50° C. to about 400° C. and the vacuum is between about 0.0001 mbar to about 3 mbar, the vacuum being measured at a location in the system between vacuum producing means and a condenser, and wherein the weight percentage of the at least one oil distillate resulting from said molecular distillation is between about 2% to about 60% out of the total weight of the at least one oil subjected to the molecular distillation; and blending the at least one distilled oil with at least one other oil, wherein the at least one other oil is optionally also subjected to the molecular distillation;

to thereby obtain an oil blend with reduced phytosterol content.

Yet, in another one of its aspects the present invention provides a process for the preparation of an oil blend having reduced phytosterol content, the process comprises:

mixing at least two oils;

subjecting the at least two oils to molecular distillation in a distillation system, wherein the molecular distillation is performed under specific temperature and vacuum conditions, and wherein the weight percentage of the at least two oils distillate resulting from the molecular distillation is between about 2% to about 60% out of the total weight of the at least two oils subjected to the molecular distillation; and optionally blending the resulted at least two oils with reduced phytosterol content with at least one further oil wherein the at least one further oil is optionally also subjected to said molecular distillation;

to thereby obtain an oil blend with reduced phytosterol content.

In yet another one of its aspects the present invention provides a process for the preparation of an oil blend having reduced phytosterol content, the process comprises:

mixing at least two oils;

subjecting the at least two oils to molecular distillation in a distillation system, wherein the system comprises vacuum generating means and at least one condenser, wherein the temperature of the at least two oils under distillation is between about 50° C. to about 400° C. and the vacuum is between about 0.0001 mbar to about 3 mbar, the vacuum being measured at a location in the system between vacuum producing means and a condenser, and wherein the weight percentage of the at least two oils distillate resulting from the molecular distillation is between about 2% to about 60% out of the total weight of the at least two oils subjected to the molecular distillation; and optionally blending the resulted at least two oils with reduced phytosterol content with at least one further oil wherein the at least one further oil is optionally also subjected to said molecular distillation;

to thereby obtain an oil blend with reduced phytosterol content.

In some embodiments the distillation system in the process according to the invention comprises vacuum generating means and at least one condenser (the latter is utilized to collect/condense the distillate) wherein the temperature of the oil or oils under distillation is between about 50° C. to about 400° C. and the vacuum is between about 0.0001 mbar to about 3 mbar, the vacuum being measured at a location in the system between vacuum producing means (e.g., a vacuum pump) and a condenser.

In some embodiments the distillation system in the process according to the invention comprises an evaporator with heating media (e.g., steam, thermal oil and the like), the evaporator having an inlet position and an outlet position, wherein the heating media being at a temperature of at least about 190° C. at the inlet position, at times about 210° C. or above, at times about 220° C. or above, at times about 230° C. or above, at times about 260° C. and above, even at times about 300° C. and above. In some embodiments the heating media is at a temperature of between about 100° C. to about 400° C., at times between about 150° C. to about 360° C., at times between about 300° C. to about 360° C., and at times between about 200° C. to about 300° C.

In some embodiments according to the process of the invention the temperature of the oil or oils under distillation is between about 100° C. to about 350° C., at times between about 200° C. to about 300° C., at times between about 100° C. to about 200° C., at times between about 150° C. to about 200° C. and at times between about 150° C. to about 190° C.

In some embodiments the distillation system in the process according to the invention comprises a condenser. In some embodiments the condenser's temperature is at most of about 90° C. At times said temperature is about 70° C. or below, at times about 60° C. or below, at times about 50° C. or below and at times about 40° C. or below.

In some embodiments according to the process of the invention the vacuum is at most of about 2 mbar. In some embodiments the vacuum is about 1 mbar or below, at times about 0.5 mbar or below, at times of about 0.1 mbar or below, at times about 0.05 mbar or below, at times 0.03 mbar or below, at times 0.02 mbar or below, at times about 0.01 mbar or below, at times 0.005 mbar or below, at times 0.001 mbar or below and at times 0.0005 mbar or below.

In some embodiments according to the process of the invention the weight percentage of the oil or oils distillate resulting from the molecular distillation is between about 2% to about 50% out of the total weight of the oil or oils subjected to the molecular distillation. At times the weight percentage of the oil or oils distillate resulting from the molecular distillation is at least about 2%. At times above 5% and even at times above 9%, 17%, 25%, 35% or 50% out of the total weight of the oil or oils subjected to the molecular distillation.

In some embodiments according to the process of the invention the weight percentage of the oil or oils distillate resulting from the molecular distillation is between about 5% to about 40%. At times the weight percentage of the oil or oils distillate resulting from the molecular distillation is between 6% to 35%, at times between 6% to 30%, at times between about 6% to about 20% and at times between about 10% to about 20% out of the total weight of the oil or oils subjected to the molecular distillation.

In some embodiments according to the process of the invention the oil or oils (e.g., at least one oil, at least two oils, at least one other oil and at least one further oil) may be any one of coconut oil, palm kernel oil, soybean oil, rapeseed oil, sunflower oil, high oleic sunflower oil, corn oil, palm olein oil, palm oil, safflower oil, high oleic safflower oil, MCT oil or sn2-palmitate oil.

In some embodiments according to the process of the invention the oil or oils (e.g., at least one oil, at least two oils, at least one other oil and at least one further oil) may be any one of coconut oil, palm kernel oil, soybean oil, rapeseed oil, sunflower oil, high oleic sunflower oil, corn oil, palm olein oil, palm oil, safflower oil, high oleic safflower oil or sn2-palmitate oil.

In some embodiments according to the process of the invention the oil or oils (e.g., at least one oil, at least two oils, at least one other oil and at least one further oil) may be a vegetable oil being any one of coconut oil, palm kernel oil, soybean oil, rapeseed oil, sunflower oil, high oleic sunflower oil, corn oil, palm olein oil, palm oil, safflower oil or high oleic safflower oil.

In some embodiments according to the process of the invention the oil or oils (e.g., at least one oil, at least two oils, at least one other oil and at least one further oil) may be any one of rapeseed oil, soybean oil or sunflower oil and wherein the weight percentage of the oil or oils distillate resulting from the molecular distillation is at least about 15% out of the total weight of the oil or oils subjected to the molecular distillation. At times said weight percentage is above about 17%, at times above about 25%, at times above about 35% and at times above about 40% out of the total weight of the oil or oils subjected to the molecular distillation.

In some embodiments according to the process of the invention the oil or oils (e.g., at least one oil, at least two oils, at least one other oil and at least one further oil) may be any one of palm kernel oil or coconut oil and wherein the weight percentage of the oil or oils distillate resulting from the molecular distillation is between about 3% to about 40% out of the total weight of the oil or oils subjected to the molecular distillation. At times said weight percentage is between about 5% to about 30%, at times between about 6% to about 30%, at times between about 6% to about 20% and at times between about 10% to about 20% out of the total weight of the oil or oils subjected to the molecular distillation.

In some embodiments the oil blends according to the invention may be obtained by utilizing column chromatography as follows: the oil (one oil or a mixture of at least two oils) may be diluted with an organic solvent (e.g., hexane, iso-hexane or a combination of the same) and loaded on a chromatography column filled with a chromatographic resin such as silica. An organic solution may then be transferred through the column. The organic solution may contain one or more solvents including but not limited to hexane, ethyl acetate and ethanol or any combination thereof. The first fraction eluted from the column may be collected, containing mostly phytosterol esters. The second fraction eluted from the column may be collected, containing the triglycerides with reduced phytosterol content (the fraction may be further subjected to evaporation/distillation means for further removal of phytosterols). The third fraction, containing mostly free sterols, may be collected by passing an organic solvent (e.g., ethyl acetate) through the column. Each of said fraction may be further processed.

In some embodiments the oil blend according to the invention (e.g., vegetable oil blend) may be obtained by controlling the oil extraction profile from oil seeds or beans. Non-limiting examples of extraction matrixes are crushed soybeans, flaked soybeans, sunflower seeds, sunflower flakes, sunflower press cake after oil was removed from it, rapeseed seeds, rapeseed press cake after pressed oil was removed. To this end, the phytosterol content of the resulted oil is reduced already at the extraction step during the production of the oil.

Thus, according to another one of its aspects the present invention provides a process for the preparation of an oil with reduced phytosterol content, the process comprises one or more means for reducing the phytosterol content of the oil during the extraction of the oil from oil-containing natural sources such as seeds, beans and flakes e.g., soybeans, sunflower seeds, rapeseed seeds, sunflower flakes and the like.

In some embodiments the oil blends according to the invention may be obtained by passing a non-polar solvent (e.g., hexane or mixture of hexane isomers such as iso hexane) through a bed of oil seeds or oil beans. The initial oil eluted containing higher levels of phytosterol esters and lower levels of free phytosterols, while the oil collected in the end of the hexane extraction elution containing the required reduced level of phytosterol esters and higher levels of free phytosterols.

In some embodiments according to the invention a polar solvent may be used, e.g. iso-propanol or ethanol and the elution profile disclosed herein in connection with hexane is reversed i.e., initial elution is composed of higher free sterols and lower sterol esters compared to the overall feed composition.

In some embodiments the oil blends according to the invention (e.g., vegetable oil blends) may be obtained by collecting different oil fractions from the different extraction stages using continues industrial extraction system.

In some embodiments the oil collected in the end of the elution may optionally be subjected to further free sterol removal by molecular distillation or other means to reach the required reduced level of the total sterol content.

In some embodiments according to the invention two or more means for reducing phytosterol levels may be applied.

In a further one of its aspects the present invention provides a process for the preparation of oil blends as herein disclosed for use as lipid ingredients in formulas such as infant formula.

In a further one of its aspects the present invention provides the oil blends as herein disclosed for use as lipid ingredients in formulas such as infant formula.

In a further one of its aspects the present invention provides the oil blends as herein disclosed for use as lipid ingredients in nutritional compositions, pharmaceutical compositions, nutraceutical compositions, parenteral nutrition composition, functional food or medical food.

In a further one of its aspects the present invention provides the oil blends as herein disclosed for use in the preparation of nutritional compositions, pharmaceutical compositions, nutraceutical compositions, parenteral nutrition composition, functional food or medical food.

A nutritional composition as used herein may be any nutritional composition including, but not limited to: human milk fat substitute, parenteral formula composition, infant formula, adult formula, dairy product, milk powder, drinks, ice cream, biscuit, soy product, bakery, pastry, bread, cake, sauce, soup, prepared food, frozen food, condiment, confectionary, oil, fat, margarine, spread, filling, cereal, instant product, infant food, toddler food, bar, snack, candy, and chocolate product.

A functional food as used herein can be any functional food, including, but not limited to: dairy product, ice-cream, biscuit, soy product, bakery, pastry, cakes and bread, instant product, sauce, soup, prepared food, frozen food, condiment, confectionary, oils and fat, margarine, spread, filling, cereal, instant product, drinks and shake, infant food, bar, snack, candy, and chocolate product.

A nutraceutical composition as used herein can be any nutraceutical, which can be any substance that may be considered as a food or part of a food and provides medical or health benefits, including the prevention and treatment of diseases or disorders. Such nutraceutical compositions include, but are not limited to: a food additive, a food supplement, a dietary supplement, genetically engineered foods (such as for example vegetables, herbal products, and processed foods such as cereals, soups, and beverages), stimulant functional food, medical food, parenteral nutrition, and pharmafood (also sometimes designated "phood"). Dietary supplements may be delivered in the form of soft gel capsules, tablets, syrups, and other known dietary supplement delivery systems.

The pharmaceutical or nutraceutical compositions may be in any of the many dosage delivery forms commonly used in the art. Pharmaceutical compositions suitable for oral administration may be presented as discrete dosage units (such as pills, tablets, pellets, dragëes, capsules, or softgel capsules), as a powder or granule, or as a liquid form, for example solution, suspension, syrup, or elixir. Solutions/suspensions may be formulated for intravenous administration.

A medical food as used herein is specially formulated and intended for the dietary management of a disease/disorder that has distinctive nutritional needs that cannot be met by normal diet alone.

In another one of its aspects the present invention provides a composition comprising an oil blend (e.g., vegetable oil blend) according to the invention for use in enteral or parenteral preparations for administration to a subject.

In another one of its aspects the present invention provides nutritional compositions, pharmaceutical compositions, nutraceutical compositions, parenteral nutrition compositions, functional food or medical food comprising an oil blend (e.g., vegetable oil blend) according to the invention for use in enteral or parenteral preparations for administration to a subject.

In another one of its aspects the present invention provides an infant formula, parenteral formula, baby food, toddler formula, child formula or adult formula comprising the oil blend (e.g., vegetable oil blend) according to the invention for use in enteral or parenteral preparations for administration to a subject.

In another one of its aspects the present invention provides a method of reducing and/or optimizing phytosterol levels in a subject, the method comprises administering to the subject an oil blend according to the invention.

In another one of its aspects the present invention provides an oil blend according to the invention for (or being used for, or being used in a method for) reducing and/or optimizing phytosterol levels in a subject.

In some embodiments the reduction and/or optimization are of the subject's phytosterol plasma level.

In another one of its aspects the present invention provides a method of reducing phytosterolemia in a subject, the method comprises administering to the subject the oil blend according to the invention.

In yet another one of its aspects the present invention provides an oil blend according to the invention for (or being used for, or being used in a method for) reducing phytosterolemia in a subject.

In another one of its aspects the present invention provides a method of reducing the risk and/or severity of parenteral nutrition-associated liver disease (PNALD) in a subject, the method comprises administering to the subject the oil blend according to the invention.

In yet another one of its aspects the present invention provides an oil blend according to the invention for (or being used for, or being used in a method for) reducing the risk and/or severity of parenteral nutrition-associated liver disease (PNALD) in a subject.

In another one of its aspects the present invention provides a method of reducing the risk and/or severity of parenteral nutrition-associated cholestasis (PNAC) in a subject, the method comprises administering to the subject the oil blend according to the invention.

In yet another one of its aspects the present invention provides an oil blend according to the invention for (or being used for, or being used in a method for) reducing the risk and/or severity of parenteral nutrition-associated cholestasis (PNAC) in a subject.

In another one of its aspects the present invention provides a method of reducing and/or optimizing bilirubin levels in a subject, the method comprises administering to the subject the oil blend according to the invention.

In yet another one of its aspects the present invention provides an oil blend according to the invention for (or being used for, or being used in a method for) reducing and/or optimizing bilirubin levels in a subject.

In some embodiments reduced and/or optimized bilirubin levels are bilirubin plasma levels.

In another one of its aspects the present invention provides method for enhancing and/or optimizing absorption of fat and/or fat soluble nutrients and/or fat soluble vitamins in a subject, the method comprises administering the oil blend (e.g., vegetable oil blend) according to the invention to the subject.

In yet another one of its aspects the present invention provides an oil blend according to the invention for (or being used for, or being used in a method for) enhancing and/or optimizing absorption of fat and/or fat soluble nutrients and/or fat soluble vitamins is a subject.

Fat soluble nutrients comprise but not limited to vitamin A, D, E or K, ascorbyl palmitate, carotenoids, carotene, lutein, zeaxanthin, lycopene, hormones and steroids.

In another one of its aspects the present invention provides method for increasing and/or optimizing dietary energy potential in a subject, the method comprises administering the oil blend (e.g., vegetable oil blend) according to the invention to the subject.

In yet another one of its aspects the present invention provides an oil blend according to the invention for (or being used for, or being used in a method for) increasing and/or optimizing dietary energy potential in a subject.

In another one of its aspects the present invention provides method for increasing and/or optimizing one or more of cholesterol, HDL cholesterol, VLDL and LDL cholesterol levels (e.g., plasma levels, levels in the liver etc.) in a subject, the method comprises administering the oil blend (e.g., vegetable oil blend) according to the invention to the subject.

In yet another one of its aspects the present invention provides an oil blend according to the invention for (or being used for, or being used in a method for) increasing and/or optimizing one or more of cholesterol, HDL cholesterol, VLDL and LDL cholesterol levels (e.g., plasma levels, levels in the liver etc.) in a subject.

In another one of its aspects the present invention provides method for optimizing one or more of LDL particles size, triglyceride levels, Apolipoprotein A levels and Apolipoprotein B levels (e.g., in the plasma or the liver) in a subject, the method comprises administering the oil blend (e.g., vegetable oil blend) according to the invention to the subject.

In yet another one of its aspects the present invention provides an oil blend according to the invention for (or being used for, or being used in a method for) optimizing one or more of LDL particles size, triglyceride levels, Apolipoprotein A levels and Apolipoprotein B levels (e.g., in the plasma or the liver) in a subject.

In another one of its aspects the present invention provides method for increasing and/or optimizing bile acid secretion in a subject, the method comprises administering the oil blend (e.g., vegetable oil blend) according to the invention to the subject.

In yet another one of its aspects the present invention provides an oil blend according to the invention for (or being used for, or being used in a method for) increasing and/or optimizing bile acid secretion in a subject.

In another one of its aspects the present invention provides method for controlling and/or optimizing bile acid levels (e.g. plasma levels) in a subject, the method comprises administering the oil blend (e.g., vegetable oil blend) according to the invention to the subject.

In yet another one of its aspects the present invention provides an oil blend according to the invention for (or being used for, or being used in a method for) controlling and/or optimizing bile acid levels (e.g. plasma levels) in a subject.

In another one of its aspects the present invention provides method for reducing and/or optimizing endogenous cholesterol synthesis in a subject, the method comprises administering the oil blend (e.g., vegetable oil blend) according to the invention to the subject.

In yet another one of its aspects the present invention provides an oil blend according to the invention for (or being used for, or being used in a method for) reducing and/or optimizing endogenous cholesterol synthesis in a subject.

In another one of its aspects the present invention provides method for optimizing and/or enhancing carotenoids absorption in a subject, the method comprises administering the oil blend (e.g., vegetable oil blend) according to the invention to the subject.

In yet another one of its aspects the present invention provides an oil blend according to the invention for (or being used for, or being used in a method for) enhancing and/or optimizing carotenoids absorption in a subject.

In another one of its aspects the present invention provides method for promoting and/or enhancing beneficial gut flora in a subject, the method comprises administering the oil blend (e.g., vegetable oil blend) according to the invention to the subject.

In yet another one of its aspects the present invention provides an oil blend according to the invention for (or being used for, or being used in a method for) promoting and/or enhancing beneficial gut flora in a subject.

In some embodiments the oil blend according to the invention is effective to promote development of gut flora comprising predominantly bifidobacteria and lactobacilli.

In another one of its aspects the present invention provides method for preventing at least one of phytosterolemia, cardiovascular diseases, hypercholesterolemia, hypertriglyceridemia, diabetes, metabolic syndrome and atherosclerosis in a subject, the method comprises administering the oil blend (e.g., vegetable oil blend) according to the invention to a subject.

In yet another one of its aspects the present invention provides an oil blend according to the invention for (or being used for, or being used in a method for) preventing at least one of phytosterolemia, cardiovascular diseases, hypercholesterolemia, hypertriglyceridemia, diabetes, metabolic syndrome and atherosclerosis in a subject.

In another one of its aspects the present invention provides method for reducing inflammation and/or CRP levels in a subject, the method comprises administering the oil blend (e.g., vegetable oil blend) according to the invention to the subject.

In yet another one of its aspects the present invention provides an oil blend according to the invention for (or being used for, or being used in a method for) reducing inflammation and/or CRP levels in a subject.

In another one of its aspects the present invention provides method for reducing and/or optimizing glucose and/or insulin levels in a subject, the method comprises administering the oil blend (e.g., vegetable oil blend) according to the invention to the subject.

In yet another one of its aspects the present invention provides an oil blend according to the invention for (or being used for, or being used in a method for) reducing and/or optimizing glucose and/or insulin levels in a subject.

In some embodiments according to the present invention each and any one of reducing and/or optimizing phytosterol levels; reducing phytosterolemia; reducing the risk and/or severity of PNALD; reducing the risk and/or severity of PNAC; reducing and/or optimizing bilirubin levels; enhancing and/or optimizing absorption of fat and/or fat soluble nutrients and/or fat soluble vitamins; increasing and/or optimizing dietary energy potential; increasing and/or optimizing one or more of cholesterol, HDL cholesterol, VLDL and LDL cholesterol levels (e.g., plasma levels, levels in the liver etc.); optimizing one or more of LDL particles size, triglyceride levels, Apolipoprotein A levels and Apolipoprotein B levels; increasing and/or optimizing bile acid secretion; controlling and/or optimizing bile acid levels (e.g. plasma levels); reducing and/or optimizing endogenous cholesterol synthesis; optimizing and/or enhancing carotenoids absorption; promoting and/or enhancing beneficial gut flora; preventing at least one of phytosterolemia, cardiovascular diseases, hypercholesterolemia, hypertriglyceridemia, diabetes, metabolic syndrome and atherosclerosis; reducing inflammation and/or CRP levels; or reducing and/or optimizing glucose and/or insulin levels, is in comparison with the subject baseline parameters.

The term "level" herein and throughout also includes "plasma level" and "tissue level" of a subject.

In some embodiments according to the present invention each and any one of reducing and/or optimizing phytosterol levels; reducing phytosterolemia; reducing the risk and/or severity of PNALD; reducing the risk and/or severity of PNAC; reducing and/or optimizing bilirubin levels; enhancing and/or optimizing absorption of fat and/or fat soluble nutrients and/or fat soluble vitamins; increasing and/or optimizing dietary energy potential; increasing and/or optimizing one or more of cholesterol, HDL cholesterol, VLDL and LDL cholesterol levels (e.g., plasma levels, levels in the liver etc.); optimizing one or more of LDL particles size, triglyceride levels, Apolipoprotein A levels and Apolipoprotein B levels; increasing and/or optimizing bile acid secretion; controlling and/or optimizing bile acid levels (e.g. plasma levels); reducing and/or optimizing endogenous cholesterol synthesis; optimizing and/or enhancing carotenoids absorption; promoting and/or enhancing beneficial gut flora; preventing at least one of phytosterolemia, cardiovascular diseases, hypercholesterolemia, hypertriglyceridemia, diabetes, metabolic syndrome and atherosclerosis; reducing inflammation and/or CRP levels; or reducing and/or optimizing glucose and/or insulin levels, is in comparison with the relevant parameter levels when a subject is administered with a conventional oil blend i.e., an oil blend which was not subjected to reductions of phytosterols.

In some embodiments the nutritional compositions, pharmaceutical compositions, nutraceutical compositions, parenteral nutrition compositions, functional food, medical food or formulas, including infant formulas, according to the invention (comprising the oil blends according to the invention) may be useful in each and any one of reducing phytosterolemia; reducing the risk and/or severity of PNALD; reducing the risk and/or severity of PNAC; reducing and/or optimizing bilirubin levels; enhancing and/or optimizing absorption of fat and/or fat soluble nutrients and/or fat soluble vitamins; increasing and/or optimizing dietary energy potential; increasing and/or optimizing one or more of cholesterol, HDL cholesterol, VLDL and LDL cholesterol levels (e.g., plasma levels, levels in the liver etc.); optimizing one or more of LDL particles size, triglyceride levels, Apolipoprotein A levels and Apolipoprotein B levels; increasing and/or optimizing bile acid secretion; controlling and/or optimizing bile acid levels (e.g. plasma levels); reducing and/or optimizing endogenous cholesterol synthesis; optimizing and/or enhancing carotenoids absorption; promoting and/or enhancing beneficial gut flora; preventing at least one of phytosterolemia, cardiovascular diseases, hypercholesterolemia, hypertriglyceridemia, diabetes, metabolic syndrome and atherosclerosis; reducing inflammation and/or CRP levels; or reducing and/or optimizing glucose and/or insulin levels.

As used herein, the term "subject" refers to a healthy subject or a subject suffering from a specific disorder (a non-healthy subject) or a subject at risk of developing a specific disorder. The subject may be a child including an infant and a toddler and an adult including a male, a female, a teenager, an elderly senior subject and a geriatric subject.

Optionally, in all aspects and embodiments of the present disclosure, the subject may be under parenteral nutrition or under partial parenteral nutrition, or a subject that cannot tolerate enteral feeding or a subject that requires non enteral feeding.

Further, the term "child" includes infants (from day of birth, newborn, to about 12 months i.e., about 1 year) as well as toddlers (from about one year up to about the age of 3).

An "infant" as used herein is meant to encompass a human infant, including but not limited to, a newborn, a very early preterm infant, a preterm infant, a term infant, a small for gestation infant and a small premature infants.

The term "newborn" includes pre-mature infants, post-mature infants and full term newborns.

In some non-limiting embodiments the subject may suffer from one or more of reduced intestinal absorption, reduced gastrointestinal function, prematurity, intestinal inflammation, celiac disease, malabsorption related to different diseases, intestinal failure, short bowel syndrome, intestinal failure secondary to short bowel syndrome, congenital absorption defects, necrotizing enterocolitis, intestinal malformations, gastrointestinal fistulas, bowel obstruction, severe acute pancreatitis, cystic fibrosis, compromised intestinal function, Crohn's disease, cancer, a condition that result from low blood flow to the bowels, conditions which relate to and/or result from parenteral nutrition.

The present invention further provides in one of its aspects phytosterols obtained in the processes disclosed herein. While reducing the phytosterol content of the oils disclosed therein, the collected phytosterols originated from the oils may be used for various purposes. For example, the phytosterols are known of their protective effect against certain types of cancer such as colon, breast and prostate, and their positive effects on benign prostatic hyperplasia. They are also known of their immune modulator, anti-inflammatory and anti-oxidative properties. Thus, apart from the beneficial effect of the oil blends disclosed herein, the by-product phytosterols produced during the preparation of the oil blends may be beneficially used.

DESCRIPTION OF NON-LIMITING EXAMPLES

Example 1: Reducing Phytosterol Levels in Soybean Oil Using Column Chromatography 30 gr of soybean oil containing 2300 ppm phytosterols and a phytosterol esters:free phytosterols ratio of about 0.2 were dissolved in 50 ml hexane, loaded on chromatography column filled with 278 grams of silica gel (Davisil, No. 1000186615, Grace Davison, Belgium) and washed with 1040 ml of hexane: ethyl acetate mixture (25:1 ratio). Elution was performed using 1680 ml of hexane: ethyl acetate mixture (25:3 ratio).

The first eluted fraction containing the phytosterol esters was collected (fraction No. 1), then the second eluted fraction containing pure TG fraction was collected (fraction No. 2). The free phytosterols remained bound to the silica.

In order to release the free phytosterols from the silica 750 ml of pure ethyl acetate were passed through the column generating fraction No. 3.

The three fractions were subjected to solvent evaporation in order to isolate the oil. The oil was analyzed for free and total phytosterols content using GC method.

Oil yield and phytosterol content in each of the three aforementioned fractions are summarized in Table 1:

TABLE 1

Oil yield and phytosterol content

| Fraction | Yield (% w/w from total oil eluted) | Phytosterol esters (as free sterols equivalent) (ppm) | Free phytosterols (ppm) |
| --- | --- | --- | --- |
| 1 | 1.3 | 118000 | — |
| 2 | 89.6 | 98 | 12 |
| 3 | 9 | — | 40000 |

Conclusion:

Fraction No. 2 represented about 90% of the eluted soybean oil and contained only about 110 ppm phytosterols, very low compared to the original content of 2300 ppm.

The phytosterol esters:free phytosterols ratio in fraction No. 2 was about 8.

Example 2: Reducing Phytosterol Levels in Soybean Oil Using Molecular Distillation and Column Chromatography 39.3 gr soybean oil containing 2620 ppm phytosterols and phytosterol esters:free phytosterols ratio of about 0.37 were fed into a lab scale molecular distillation unit (Pope) with an evaporator having an inlet position and an outlet position with the following parameters: 230° C. inlet temperature of the evaporator heating media, 0.01 mbar pressure, 70° C. condenser temperature. Residue fraction and distillate fraction were collected.

The residue was analyzed for free and total phytosterol content by GC method and was found to contain only 622 ppm phytosterols.

Additional removal of phytosterols from the residue fraction was obtained by dissolving the fraction with 50 ml of hexane and loading on a chromatography column filled with 278 grams of silica gel (Davisil, No. 1000186615, Grace Davison, Belgium). The column was washed with 1040 ml hexane: ethyl acetate mixture (25:1 ratio) and elution was performed using 1680 ml hexane: ethyl acetate mixture (25:3 ratio).

The first eluted fraction containing the phytosterol esters, was collected (fraction No. 1), then the second eluted fraction containing pure TG (fraction No. 2) was collected and the free phytosterols remained bound to the silica.

In order to release the free phytosterols from the silica 750 ml of pure ethyl acetate were transferred through the column generating fraction No. 3.

The three fractions were subjected to solvent evaporation in order to isolate the oil. The oil was analyzed for free and total sterol content using GC method.

Oil yield and phytosterol content in each of the aforementioned three fractions are summarized in Table 2:

TABLE 2

Oil yield and phytosterol content

| Fraction | Yield (% w/w from total oil eluted) | Phytosterol esters (as free sterols equivalent) (ppm) | Free phytosterols (ppm) |
|---|---|---|---|
| 1 | 3.3 | 27000 | — |
| 2 | 90.3 | 60 | — |
| 3 | 6.3 | — | <2000 |

Example 3: Preparation of Vegetable Soybean and Rapeseed Oils Blend According to the Present Invention Using Molecular Distillation Soybean oil with about 2620 ppm phytosterols and rapeseed oil with 8400 ppm were treated separately using a molecular distillation unit as described in Example 2 above.

The resulting soybean and rapeseed oils, which contained 622 ppm and 2960 ppm of phytosterols, respectively and phytosterol esters:free phytosterols ratio of 10.5 and 3, respectively, were mixed in 1:1 ratio to obtain an oil blend containing 1791 ppm phytosterols and phytosterol esters:free phytosterol ratio of 30.

Example 4: Preparation of Vegetable Oil Blends According to the Present Invention Using Molecular Distillation Rapeseed oil, high oleic sunflower oil (HOSO), palm oil, coconut oil, palm kernel oil, soybean oil and sunflower oil were each treated using lab scale molecular distillation unit (VKL 70-4, VTA company, Germany) to reduce their phytosterol level.

Each oil was fed (separately) into a heated feed vessel at 50° C. and pumped into a wiped film evaporator (degassing stage) to remove water and air residues at 4.7 mbar and 160° C. Following degassing stage the oil was pumped into the short path distillation stage at feed rate of approximately 300 gr/h. Short path evaporator (having an inlet position and an outlet position) was operated under vacuum of approximately 0.02 mbar and temperature as specified in Table 3.

Table 3 demonstrates that the residues (bottom fractions) from distillation contained oils with reduced amount of phytosterols. It further demonstrates that while most oils showed reduced phytosterol content of the residue with increased distillate weight percentages, palm kernel oil and coconut oil distillation were most efficient in reducing phytosterol content within a specific range of distillate weight percentage. Specifically, between about 6% to about 21% distillate weight for palm kernel oil and between 6% and 30% distillate weight for coconut oil out of total oil weight.

TABLE 3 distillation conditions of different oils

| | Phytosterol content before distillation (ppm) | Inlet temperature of the evaporator heating media (° C.) | % Distillate (w/w) out of total oil weight | Phytosterol content following distillation (ppm) | % phytosterol removal |
|---|---|---|---|---|---|
| Rapeseed | 8484 | 260 | 2.6 | 4231 | 50.0 |
| | | 270 | 4.9 | 4041 | 50.0 |
| | | 280 | 8.9 | 2976 | 65.0 |
| | | 290 | 17.6 | 1964 | 77.0 |
| | | 295 | 25.2 | 1566 | 82.0 |
| | | 300 | 37.1 | 1048 | 87.5 |
| Palm Kernel oil | 1007 | 185 | 1.5 | 570 | 43.4 |
| | | 195 | 3.2 | 456 | 54.7 |
| | | 205 | 6.3 | 371 | 63.2 |
| | | 215 | 11.4 | 330 | 67.2 |
| | | 225 | 20.5 | 345 | 65.7 |
| Coconut oil | 476 | 185 | 3.2 | 348 | 26.9 |
| | | 195 | 6.1 | 290 | 39.1 |
| | | 205 | 11.9 | 288 | 39.5 |
| | | 215 | 21.2 | 276 | 42.0 |
| | | 225 | 35.8 | 300 | 37.0 |
| | | 235 | 44.5 | 344 | 27.7 |

TABLE 3-continued distillation conditions of different oils

| | Phytosterol content before distillation (ppm) | Inlet temperature of the evaporator heating media (° C.) | % Distillate (w/w) out of total oil weight | Phytosterol content following distillation (ppm) | % phytosterol removal |
|---|---|---|---|---|---|
| Soybean oil | 2699 | 250 | 2.2 | 710 | 73.7 |
| | | 260 | 2.9 | 669 | 75.2 |
| | | 270 | 5 | 571 | 78.8 |
| | | 280 | 8.9 | 480 | 82.2 |
| | | 290 | 19 | 340 | 87.4 |
| | | 300 | 39.4 | 262 | 90.3 |
| Sunflower oil | 1680 | 250 | 1.7 | 568 | 66.2 |
| | | 260 | 2.7 | 486 | 71.1 |
| | | 280 | 8.7 | 381 | 77.3 |
| | | 290 | 17.4 | 272 | 83.8 |
| | | 300 | 36 | 145 | 91.4 |

Example 5: Stability of Vegetable Oil Blends According to the Invention in Comparison with Conventional (not Phytosterol-Reduced) Vegetable Oil Blend Rapeseed oil, high oleic sunflower oil and palm oil were treated using a pilot scale molecular distillation unit (VK 125-15, VTA company, Germany) to reduce their phytosterols level.

Each oil was fed into a heated feed vessel at 50° C. and then pumped into a wiped film evaporator (degassing stage) to remove water and air residues (5 mbar & 170° C.). Following the degassing stage the oil was pumped into the short path distillation stage.

Short path evaporator was operated with the following conditions:

Vacuum of about 0.02 mbar, feed rate of about 12 kg/hr, inlet temperature of the evaporator heating media of about 312° C. for rapeseed oil, high oleic sunflower oil and soybean oil, 293° C. for palm oil and 215° C. for coconut oil and distillate weight % of about 40% for rapeseed oil, high oleic sunflower oil and soybean oil, about 30% for palm oil and about 10% for coconut oil.

The residues (bottom fraction) from distillation contain lower phytosterol levels.

Phytosterol levels before and after the molecular distillation process are summarized in Table 4.

TABLE 4

Phytosterol level in vegetable oils before and after phytosterol reduction

| | Rapeseed oil | High oleic sunflower oil | Palm oil | Soybean oil | Coconut oil |
|---|---|---|---|---|---|
| Phytosterol content of conventional (prior phytosterol reduction) refined oil (ppm) | 7074 | 1599 | 535 | 2699 | 476 |
| Vegetable distilled oil temperature (° C.) | 178.2 | Not measured | 149.7 | Not measured | Not measured |

TABLE 4-continued

Phytosterol level in vegetable oils before and after phytosterol reduction

| | Rapeseed oil | High oleic sunflower oil | Palm oil | Soybean oil | Coconut oil |
|---|---|---|---|---|---|
| Phytosterol content of oils with reduced phytosterol content (ppm) | 1171 | 194 | 161 | 193 | 307 |

Four different oil blends (Blend 1 to 4) were prepared following heating each oil to 40° C. as described in Table 5.

Blend 1 (a blend of phytosterol reduced rapeseed and palm oils);

Blend 2 (a blend of conventional rapeseed and palm oils);

Blend 3 (a blend of phytosterol reduced rapeseed and high oleic sunflower oils); and Blend 4 (a blend of conventional rapeseed and high oleic sunflower oils).

TABLE 5

Preparation of oil blends

| | Blend 1 | Blend 2 | Blend 3 | Blend 4 |
|---|---|---|---|---|
| Conventional (prior phytosterol reduction) rapeseed oil (gr) | | 10 | | 10 |
| Rapeseed oil with reduced phytosterol content (gr) | 10 | | 10 | |
| Conventional (prior phytosterol reduction) high oleic sunflower (gr) | | | | 10 |
| High oleic sunflower oil with reduced phytosterol content (gr) | | | 10 | |

TABLE 5-continued

Preparation of oil blends

|  | Blend 1 | Blend 2 | Blend 3 | Blend 4 |
|---|---|---|---|---|
| Conventional (prior phytosterol reduction) palm oil (gr) |  | 10 |  |  |
| Palm oil with reduced phytosterol content (gr) | 10 |  |  |  |

Stability of all four blends was tested following incubation at 40° C. for six days using peroxide value (PV) measurements. The results of the stability test are summarized in Table 6.

TABLE 6

PV values of oil blends following six days incubation at 40° C.

| Blend No. | PV (meq Koh/kg) |
|---|---|
| Blend 1 (a blend of phytosterol reduced rapeseed and palm oils) | 2.4 |
| Blend 2 (a blend of conventional rapeseed and palm oils) | 2.9 |
| Blend 3 (a blend of phytosterol reduced rapeseed and high oleic sunflower oils) | 4.4 |
| Blend 4 (a blend of conventional rapeseed and high oleic sunflower oils) | 5.9 |

As demonstrated in Table 6, phytosterol reduced oil blend according to the invention demonstrated 17%-25% reduction in the peroxide value in comparison with the corresponding conventional oil blends (blend 1 vs. blend 2 and blend 3 vs. blend 4). This result is indicative of the greater stability of oil blends with reduced phytosterol levels, according to the invention, in comparison with conventional oil blends.

Example 6: Production and Properties of Infant Formulas Containing Conventional (not Phytosterol Reduced) Vegetable Oil Blends and Infant Formulas Containing Vegetable Oil Blends According to the Invention A. Infant Formulas Production:

Four infant formulas were produced using the following method:

102 kg water were inserted into a heated 50-55° C. tank with an agitator at 40 RPM. Then, the components specified in Table 7 were added.

TABLE 7

Infant formula components

| Components | Weight (kg) |
|---|---|
| Lactose | 20.89 |
| Demineralized whey powder | 27 |
| Skimmed milk powder | 13.23 |
| Whey protein concentrate 80 | 3.36 |
| Vit premix FPS152 v1 | 0.18 |
| Min premix FPS136A | 0.09 |
| Ascorbic acid | 0.45 |
| Choline Chloride | 0.258 |
| $MgCl_2 \times 6H_2O$ | 0.78 |
| $FeSO_4 \times 7H_2O$ | 0.0825 |
| $Na_3Cit \times 2H_2O$ | 1.32 |
| $CaCO_3$ | 0.75 |
| DKP (potassium hydrogen phosphate) | 0.57 |

TABLE 7-continued

Infant formula components

| Components | Weight (kg) |
|---|---|
| $DCP \times 2H_2O$ | 1.17 |
| KCl | 0.63 |
| Calcium hydroxide | 0.24 |
| Citric acid | 0.09 |
| Taurine | 0.138 |

Finally, after preheating to 40° C., 23.67 kg of one of the oil blends described in Table 8 were added to the tank.

TABLE 8 composition of oil blends

|  | Oil Blend # 483-27* | Oil Blend # 483-26** | Oil Blend # 483-23* | Oil Blend # 483-25** |
|---|---|---|---|---|
| C8:0% (w/w) out of oil | 0.6 | 1.2 | 0.6 | 1.2 |
| C10:0% (w/w) out of oil | 0.5 | 1.0 | 0.5 | 1.0 |
| C12:0% (w/w) out of oil | 7.4 | 7.4 | 7.1 | 7.6 |
| C14:0% (w/w) out of oil | 2.9 | 3.2 | 2.9 | 3.3 |
| C16:0 (w/w) out of oil | 19.7 | 18.8 | 20.7 | 19.3 |
| C18:0 (w/w) out of oil | 2.9 | 3.9 | 2.9 | 3.9 |
| C18:1 (w/w) out of oil | 37.9 | 35.2 | 35.9 | 34.6 |
| C18:2 (Linoleic) (w/w) out of oil | 18.6 | 17.6 | 17.4 | 17.1 |
| C18:3 (alpha-Linolenic) (w/w) out of oil | 2.2 | 1.9 | 2.0 | 1.8 |
| ***Free cholesterol (kg) |  |  | 0.057 | 0.059 |
| Esterified cholesterol (kg) |  |  | 0.026 | 0.025 |

*Oil blends were prepared from the conventional vegetable oils described in Example 5 (Table 4).
**Oil blends were prepared from the phytosterol reduced vegetable oils described in Example 5 (Table 4).
***Free cholesterol was added to one of the oils of each blend after its prior heating to about 60° C.

After all the materials were added to the tank, a homogenization stage was operated (stage 1—200 bar, stage 2—50 bar). Then, the mixture was cooled down to 12-15° C. and transferred through an in-line pasteurization stage at 70° C. for several seconds. The mixture was then fed into the spray dryer (40 liter/hr., 190° C. air inlet, 90° C. air outlet) connected in series to a fluidized bed (70° C.). Dried material was packed in 3 kg bags, flashed with nitrogen and heat sealed. The four formulas were marked according to their oil blend number (i.e., 483-23, 483-25, 483-26, 483-27 as detailed in Table 8). The infant formulas composition is described in Table 9.

TABLE 9 infant formulas composition

| /100 gr formula | | 483- 27 (Control- standard infant formula) | 483- 26 (Infant formula with the vegetable oil blend invention) | 483- 23 (Control- infant formula with standard oil blends and added cholesterol) | 483- 25 (Infant formula with the vegetable oil blend of the invention and added cholesterol) |
|---|---|---|---|---|---|
| Energy | kJ | 2148 | 2141 | 2149 | 2141 |
|  | kCal | 513 | 512 | 514 | 512 |
| Protein | g | 12 | 12 | 11.9 | 11.9 |
| Fat | g | 26.6 | 26.5 | 26.7 | 26.5 |
| Carbohydrate | g | 56.5 | 56.3 | 56.4 | 56.4 |
| Moisture | g | 2.22 | 2.53 | 2.3 | 2.52 |
| Ash | g | 2.7 | 2.64 | 2.67 | 2.67 |
| Cholesterol | mg | 17.4 | 16.0 | 66.4 | 62.1 |
| Phytosterols | mg | 60 | 7.1 | 69 | 6.4 |

A. Wettability Test:

Infant Formula samples 483-23-IF and 483-25-IF were tested for wettability [the rate at which powder particles become wetted (sink below the surface of the water and any remaining on the surface adopt typical wet appearance)] and free fat (the amount of fat that ends up on the surface of the powder particles instead of being "trapped" within its core). As demonstrated in Table 10 the infant formula which contained a vegetable oil blend according to the invention had better wettability (19% faster wettability) in comparison with infant formula containing a conventional vegetable oil blend. In addition, less free fat (7%) was measured in the infant formula which contained a vegetable oil blend according to the invention in comparison with infant formula containing a conventional vegetable oil blend.

TABLE 10

Wettability and free fat

|  | 483-23-IF (Control- infant formula with standard oil blends) | 483-25-IF (Infant formula containing the vegetable oil blend of the invention) |
|---|---|---|
| Wettability (Sec) | 21 | 17 |
| Free fat (% w/w) | 0.6 | 0.56 |

Example 7: The Effect of Different Phytosterol Levels in Infant Formulas on Fatty Acid Release The effect of different phytosterol levels in infant formulas on free fatty acids release during digestion was examined in an in vitro model of intestine, pH stat. This model is used to monitor the lipolysis rate and extent. The pH stat methodology was done using an auto-titration unit (Titrando 902, Metrohm, Switzerland) in a heated jacketed reactor (maintained at 37° C.), continuously stirred (230 RPM) with pH held constant at pH=7.00. This was done using "TIAMO 2.3" software (Metrohm, Switzerland) and controlled volumes of 50 mM NaOH, based on previous reports [10].

1 gr formula No. 483-26-IF and 1 gr formula No. 483-27-IF were mixed with 6 ml of purified water until fully homogenized solutions were achieved. 4 ml of each solution were tested separately in the gut model system which included bile extract and $CaCl_2$ solution. Eventually, a freshly prepared lipase solution containing lipase was added. pH=7 was adjusted using minimal volumes of HCl and NaOH solutions using 1 M, 0.5 M and 0.05 M, as needed. Once the lipase solution was added to the reactor the pH stat control program was initiated.

The percentage of free fatty acids (FFAs) released during pH stat lipolysis was determined through the amount of NaOH that was added to the reactor.

Results

Figure 3:
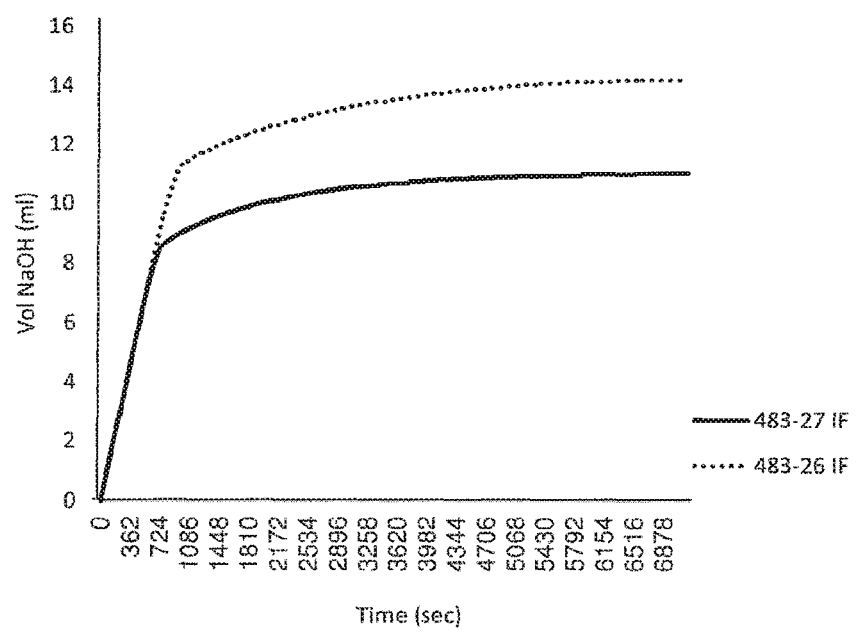
FIG. 3 illustrates an embodiment of the invention according testing the effect of different phytosterol levels in infant formulas on free fatty acids release. The figure depicts the lipolysis profile of the tested samples.

The results of the pH stat represent the lipolysis of the different lipids (triglyceride mixtures). The quality of lipolysis was examined in mean of total lipolysis. The lipolysis profile of the samples is shown in FIG. 3.

The results demonstrate that sample "483-26 IF" (Infant Formula 483-26-IF) according to the invention underwent lipolysis to a higher extent compared to the Infant formula with higher phytosterols level (sample "483-27 IF" i.e., Infant Formula 483-27-IF). This may indicate a better digestive potential for the oil blend of the invention.

Example 8: The Effect of Different Oil Blends on the Lipids Absorption and Blood Profile in an Animal Model Study Design:

The bioavailability of different oil blends is investigated in an animal model of neonatal Sprague Dawley rats aged 3-5 days. Animals are randomly assigned to one of the four diets detailed herein below, twelve rats per group. Animals within a litter are randomly assigned across treatments.

The study groups are:

Group A: Formula containing standard (not phytosterol reduced) vegetable oils blend.

Group B: Formula containing standard (not phytosterol reduced) vegetable oils blend enriched with cholesterol.

Group C: Formula containing vegetable oils blend with reduced phytosterol content according to the present invention.

Group D: Formula containing vegetable oils blend with reduced phytosterol content according to the present invention enriched with cholesterol.

All diets are essentially similar with respect to nutrient content including fatty acid composition and differ only in the level of cholesterol and phytosterols.

Gastrostomy Tube Fed Infant Rats:

The gastrostomy tube fed rat pup is a model mimicking infants fed formula, using tube feeding to overcome the difficulties in bottle-feeding of neonatal rats. The milk formulas are based on rat milk. The model enables complete control of the volume and thus nutrient intake. This avoids any difficulties due to variable intake across treatment groups. The animals are reared by milk feeding from 3-5 to 18-20 days of age. Milk volume is calculated daily based on the animal weight.

Analyses:

Blood samples are centrifuged at 2000 g×10 minutes, and plasma is recovered. Plasma is analyzed for: VLDL+LDL cholesterol, HDL cholesterol, TAG, fatty acids, fat soluble vitamins.

Results:

Group C demonstrates increased plasma cholesterol and fat soluble vitamin levels in comparison with group A and group D demonstrates increased plasma cholesterol levels in comparison with groups A and B.

Conclusion:

The above results demonstrate that rats consuming formula according to the invention (Groups C and D) have higher plasma cholesterol and fat soluble vitamin levels in comparison with rats consuming conventional formula (Group A).

Example 9: The Effect of Different Oil Blends on the Lipids Absorption and Blood Profile in a Newborn Piglet Model The aim of this study was to investigate the effect of infant formula with phytosterol-reduced vegetable oils in comparison with infant formula with conventional vegetable oils on different parameters using the neonate piglet as a model for the human infant.

Experimental Design:

Thirty two male piglets (approximately 1 week of age) were housed in purpose-built plastic metabolism crates in a temperature controlled room maintained at 28±2° C. with a 16:8 hours light: dark cycle. The piglets were initially weighed and their daily formula ration calculated as 345 g prepared liquid formula per kg bodyweight per day. The piglets were randomly allocated to one of the four dietary treatments (8 piglets per group): (a) control standard infant formula (483-27-IF, See Example 6), (b) infant formula containing a vegetable oil blend according to the invention (483-26-IF, See Example 6), (c) standard infant formula with added cholesterol (483-23-IF, See Example 6), (d) infant formula containing a vegetable oil blend according to the invention with added cholesterol (483-25-IF, See Example 6). The piglets were trained to drink using a bottle and teat and during the first 6 days were fed hourly from 06:00 h to 22:00 h. From day 7 to 21 of the trial period the pigs received their daily ration as 7 meals fed at 2.5 hr intervals from 06:30 h to 21:30 h. The pigs were weighed and their daily ration adjusted accordingly. From day 13 to 21, 0.3% titanium dioxide was added to the formulas as an indigestible marker. The inclusion of the marker from day 13-21 permits the option of using the total faecal collection method or the spot sampling method (which requires an indigestible marker in the diet) for determining faecal cholesterol digestibility. On day 16 ostomy bags were fitted to the piglets for faecal collection and faeces were collected from days 17-21 inclusive.

On day 21 of the study, the piglets were fed their respective formula at hourly intervals starting at 06:30 h. Seven hours after the start of feeding each piglet was anaesthetised, a blood sample taken, and the piglets then euthanized and the last 20 cm of small intestine (terminal ileum) dissected out. Digesta was flushed from the dissected ileum, collected and freeze dried. In addition, a sample of liver tissue and two small intestinal tissue samples (one immediately anterior to the dissected terminal ileal section and one from the duodenum) were taken and frozen at −80° C., the digesta was freeze-dried and plasma was prepared from the blood. The total list of analyses is as follows:

Blood parameters:
glucose
serum total cholesterol
HDL cholesterol
LDL cholesterol
triglyceride content
total blood bile salts
Plasma cholesterol precursors and non-cholesterol sterol levels
Plasma fat soluble vitamin concentrations
Apolipoproteins A, B,
LDL size (small particles)
Antioxidant capacity: total antioxidants, lipid peroxides, ascorbate, 8-isoprostane and thiobarbituric acid reactive substances (TBARS)
CRP
Insulin
Feces parameters:
Stool total fat
fecal cholesterol
Digesta parameters:
Cholesterol in Ileal digesta
Bile acids in Ileal digesta
Tissue parameters:
Cholesterol and sterols in liver, proximal and distal intestine Results:

The piglets fed the infant formula with the vegetable oil blend according to the invention, demonstrated higher cholesterol, LDL cholesterol and improved bile salt levels in the blood. Furthermore the results indicate that the lipid of the invention enables significant cholesterol levels increase with the addition of cholesterol to the formula and reduced blood glucose levels and VLDL blood levels.

Additionally, those piglets fed with the oil blend according to the invention demonstrate:

lower endogenous cholesterol synthesis (lower levels of cholesterol precursors; Δ8-cholestenol, lathosterol, and desmosterol)
Higher fat soluble vitamin concentrations
Lower stool total fat, meaning better fat absorption
Lower fecal cholesterol, pointing of higher absorption
Higher HDL cholesterol
Lower CRP
Decreased Insulin
Increased cholesterol levels in the intestine (villous) liver
Lower levels of hepatic HMG-CoA reductase activity (less endogenous cholesterol production)
A more beneficial gut bacteria (higher positive bacteria and less pathogenic bacteria)

Conclusion:

The cholesterol from the formula with the oil blend of the invention (b and d) is better absorbed (compared to a and c, respectively) thus the cholesterol plasma level is higher compared to the control. Moreover, this oil blend enables better absorption of fat and fat soluble vitamins. This benefit is of high importance for infant nutrition and even to a higher extent in small infant and preterm infants as the level of the pancreatic lipase is limited in those infants.

The lower endogenous cholesterol production might be related to later in life lower rate of production and lower risk for metabolic syndrome and atherosclerosis.

Thus, the oil blend of the invention with reduced phytosterols provides the subject with more efficient bioavailability of cholesterol, triglycerides and vitamins.

Example 10: The Effect of the Oil Blend of the Invention on Cholestasis in Rats Nourished Parenterally Study Design:

Male Wistar rats are divided in two groups:
1. Animals infused with total parenteral nutrition (TPN) containing a common oil blend emulsion.
2. Animals infused with TPN containing the oil blend of the invention with reduced phytosterols level.

Diets are isocaloric and differ in their phytosterols levels only.

The animals, are housed in individual room with controlled temperature and light conditions, and have open access to food.

Blood samples are analyzed for liver function tests, lipid profile, and bile acids. Liver samples (4-6 μm) are fixed and analyzed.

Results and Conclusions:

The study demonstrates the benefits of the oil blend of the invention. The animals infused with the oil blend according to the invention show less cholestasis and liver damage as lower levels of liver enzymes (ALP), bilirubin levels and serum bile acid levels are seen in the animals that are infused with the oil blend of the invention compared to the control.

Example 11: The Effect of Different Oil Blends on the Lipids Absorption and Blood Profile in Healthy Term Infants A double blind controlled clinical study is done to examine the effect of different blends of vegetable oils on the lipid profile of healthy term infants. The oil blends are mixtures of vegetable oils to provide fatty acids composition close to the fatty acids composition of human milk fat.

Study Design:

The effect of the fat component in the infant formula on plasma lipid profile is examined in a double blind randomized clinical trial in human term formula fed infants with a reference arm of human breastfed infants.

Following screening, 90 healthy, growing, term infants are randomized to one of three formula groups detailed herein below, with additional 30 breastfed infants as reference. Infants are fed according to the groups until age of 4 months.

Blood samples are taken at 8 weeks and at 4 months postnatal.

Diets:

The four study groups are:

Group I—Infants fed conventional (not phytosterol reduced) infant formula.

Group II—Infants fed infant formula according to the invention with reduced phytosterol content.

Group III—Infants fed infant formula according to the invention with reduced phytosterol content enriched with 100 mg/L cholesterol.

Group IV—Infants fed human milk.

The infant formula groups (I-III) are essentially similar with respect to nutrient content and fatty acid composition and differ only in the level of cholesterol and phytosterols.

Table 11 provides the diet fat composition comparison between tested groups (% of weight of total fatty acids).

TABLE 11

Diet fat composition comparison between tested Groups (% of weight of total fatty acids)

| Fatty acid | Group I Regular Infant Formula | Group II infant formula according to the invention with reduced phytosterol content | Group III infant formula according to the invention with reduced phytosterol content enriched with cholesterol | Group IV Human milk |
|---|---|---|---|---|
| C8:0 | 0.9 | 0.9 | 0.9 | |
| C10:0 | 0.8 | 0.8 | 0.8 | 0.05-2.21 |
| C12:0 | 10.4 | 10.4 | 10.4 | 2.01-11.77 |
| C14:0 | 4.3 | 4.3 | 4.3 | 2.26-11.68 |
| C16:0 (Ratio*) | 22.3 (43%) | 22.3 (43%) | 22.3 (43%) | 12.9-27.50 |
| C18:0 | 4.4 | 4.4 | 4.4 | 3.49-10.65 |
| C18:1 | 38.5 | 38.5 | 38.5 | 23.55-55.25 |
| C18:2 | 14.0 | 14.0 | 14.0 | 5.79-27.55 |
| C18:3 | 1.5 | 1.5 | 1.5 | 0.25-1.9 |
| C20:4 | 0.5 | 0.5 | 0.5 | 0.05-0.87 |
| C22:6 | 0.4 | 0.4 | 0.4 | 0-1.03 |
| Cholesterol | <40 mg/L | <40 mg/L | 100 mg/L | 100-200 mg/L |

*"Ratio" represents % of C16:0 at sn-2 palmitic acid out of total C16:0.

Blood samples taken at 8 weeks and at 4 months postnatal are analyzed for total cholesterol, VLDL+LDL cholesterol, HDL cholesterol, TAG, fatty acids, fat soluble vitamins (vitamin A, D, E and K).

Group II and III demonstrate increased plasma cholesterol and fat soluble vitamins levels compared with Group I and similar to the levels of group IV.

Conclusion:

The above results demonstrate that healthy term infants consuming formula which contains the composition of the invention (Groups II and III) have cholesterol and fat soluble vitamins levels which are more similar to those of breastfed infants and higher in comparison with infants consuming conventional infant formulas (Group I).

Example 12: The Effect of the Oil Blend of the Invention on Cholestasis in Preterm Infants Nourished Parenterally Study Design:

In this double blind study preterm infants are randomly divided in two groups:
1. Infused with TPN containing a common oil blend emulsion.
2. Infused with TPN containing the oil blend of the invention with reduced phytosterols level.

Diets are isocaloric with same sources of oils and same fatty acids composition and differ in their phytosterols levels only.

Blood samples are analyzed for liver function tests, lipid profile, and bile acids.

Results and Conclusions

The study demonstrates the benefits of the oil blend of the invention. The infants infused with this oil blend show less cholestasis and liver damage as lower levels of bilirubin, GGT, alkaline phosphatase, AST, ALT and normal serum bile acid levels are seen compared to the infants infused with the control.

What is claimed is:

1. An infant formula which comprises an oil blend comprising at least two oils, each of which two oils has a reduced phytosterol level compared to such oil prior to reducing its phytosterol content, wherein at least one of the two oils is MCT oil or sn2-palmitate oil having a phytosterol content of less than 300 ppm; and the other of the two oils is selected from the following:
coconut oil having a phytosterol content of less than 450 ppm;
palm kernel oil having a phytosterol content of less than 900 ppm;
soybean oil having a phytosterol content of less than 1800 ppm;
rapeseed oil having a phytosterol content of less than 5800 ppm;
sunflower oil having a phytosterol content of less than 1600 ppm;
high oleic sunflower oil having a phytosterol content of less than 1500 ppm;
corn oil having a phytosterol content of less than 5900 ppm;
palm olein oil having a phytosterol content of less than 700 ppm;
palm oil having a phytosterol content of less than 530 ppm;
safflower oil having a phytosterol content of less than 8500 ppm; or
high oleic safflower oil having a phytosterol content of less than 1000 ppm,
and wherein the fatty acid composition of the infant formula is as follows:
0-10% C8:0 fatty acids out of the total fatty acids;
0-10% C10:0 fatty acids out of the total fatty acids;
0-22% C12:0 fatty acids out of the total fatty acids;
0-15% C14:0 fatty acids out of the total fatty acids;
5-55% C16:0 fatty acids out of the total fatty acids;
1-7% C18:0 fatty acids out of the total fatty acids;
20-75% C18:1 fatty acids out of the total fatty acids;
2-40% C18:2 fatty acids out of the total fatty acids;
0-8% C18:3 fatty acids out of the total fatty acids; and
Other fatty acids present in levels of less than 8% of the total fatty acids.

2. An infant formula which comprises an oil blend comprising at least two oils wherein at least one of the two oils is MCT oil or sn2-palmitate oil, and the other of the two oils is selected from the following: coconut oil, palm kernel oil, soybean oil, rapeseed oil, sunflower oil, high oleic sunflower oil, corn oil, palm olein oil, palm oil, safflower oil, or high oleic safflower oil, wherein the total phytosterol content in ppm of said oils within the blend is below the value obtained using the following formula (I)

$$\left[\sum_{n=1}^{13} (X_n * K_n)\right] / 100 \quad \text{Formula (I)}$$

wherein
n is an integer of 1 to 13 and represents the number of said specific oils;
$X_n$ represents the percent by weight of a specific oil out of the total weight of said n specific oils;
$K_n$ represents a pre-determined threshold value of phytosterol content in ppm of a specific oil which value is reduced compared to the phytosterol content of said oil in ppm prior to reducing its phytosterol content;
wherein said pre-determined threshold values of phytosterol contents of the specific oils ($K_n$) are the following:

| Oil | $K_n$ |
|---|---|
| coconut oil | 450 |
| palm kernel oil | 900 |
| soybean oil | 1800 |
| rapeseed oil | 5800 |
| sunflower oil | 1600 |
| high oleic sunflower oil | 1500 |
| corn oil | 5900 |
| palm olein oil | 700 |
| palm oil | 530 |
| safflower oil | 8500 |
| high oleic safflower oil | 1200 |
| MCT oil | 1000 |
| sn2-palmitate oil | 300 | and wherein the fatty acid composition of the infant formula is as follows:
0-10% C8:0 fatty acids out of the total fatty acids;
0-10% C10:0 fatty acids out of the total fatty acids;
0-22% C12:0 fatty acids out of the total fatty acids;
0-15% C14:0 fatty acids out of the total fatty acids;
5-55% C16:0 fatty acids out of the total fatty acids;
1-7% C18:0 fatty acids out of the total fatty acids;
20-75% C18:1 fatty acids out of the total fatty acids;
2-40% C18:2 fatty acids out of the total fatty acids;
0-S % C18:3 fatty acids out of the total fatty acids; and
Other fatty acids present in levels of less than 8% of the total fatty acids.

3. The infant formula of claim 1, wherein the:
coconut oil comprises a ratio of phytosterol esters: free phytosterols of greater than 0.6;
palm kernel oil comprises a ratio of phytosterol esters: free phytosterols of greater than 0.6;
soybean oil in which the comprises a ratio of phytosterol esters: free phytosterols of greater than 0.5;
rapeseed oil comprises a ratio of phytosterol esters: free phytosterols of greater than 1.7;
sunflower oil in which the comprises a ratio of phytosterol esters: free phytosterols of greater than 0.7;
high oleic sunflower oil comprises a ratio of phytosterol esters: free phytosterols of greater than 0.7;
corn oil comprises a ratio of phytosterol esters: free phytosterols of greater than 1.8;
palm olein oil comprises a ratio of phytosterol esters: free phytosterols of greater than 0.4;
palm oil comprises a ratio of phytosterol esters: free phytosterols of greater than 1;
safflower oil comprises a ratio of phytosterol esters: free phytosterols of greater than 1.1;
high oleic safflower oil comprises a ratio of phytosterol esters: free phytosterols of greater than 1.3;
MCT oil comprises a ratio of phytosterol esters: free phytosterols of greater than 0.5; or
sn2-palmitate oil comprises a ratio of phytosterol esters: free phytosterols of greater than 0.9.

4. The infant formula of claim 1, wherein the ratio between phytosterol esters concentration in ppm of said oils within the blend is above the result obtained using the following formula (IV):

$$0.01 * \left[\sum_{n=1}^{13} (X_n * R_n * K_n)\right] / \left[\sum_{n=1}^{13} (K_n)\right] \quad \text{Formula (IV)}$$

wherein n is an integer of 1 to 13 and represents the number of said specific oils;

$X_n$ represents the percent by weight of a specific oil out of the total weight of said n specific oils;

$R_n$ represents a pre-determined threshold value of the ratio between the phytosterol ester concentration (in ppm) and the free phytosterol concentration (in ppm) in the specific oil;

$K_n$ represents a pre-determined threshold value of phytosterol content in ppm of said specific oil which value is reduced compared to the phytosterol content of said oil in ppm prior to reducing its phytosterol content;

and wherein said pre-determined threshold value of the ratio between phytosterol esters concentration in ppm and free phytosterols concentration in ppm in the specific oils ($R_n$) are the following:

| Oil | $R_n$ |
| --- | --- |
| coconut oil | 0.6 |
| palm kernel oil | 0.6 |
| soybean oil | 0.5 |
| rapeseed oil | 1.7 |
| sunflower oil | 0.7 |
| high oleic sunflower oil | 0.7 |
| corn oil | 1.8 |
| palm olein oil | 0.4 |
| palm oil | 1 |
| safflower oil | 1.1 |
| high oleic safflower oil | 1.3 |
| MCT oil | 0.5 |
| sn2-palmitate oil | 0.9 | and wherein said pre-determined threshold value of phytosterol contents of the specific oils ($K_n$) are the following:

| Oil | $K_n$ |
| --- | --- |
| coconut oil | 450 |
| palm kernel oil | 900 |
| soybean oil | 1800 |
| rapeseed oil | 5800 |
| sunflower oil | 1600 |
| high oleic sunflower oil | 1500 |
| corn oil | 5900 |
| palm olein oil | 700 |
| palm oil | 530 |
| safflower oil | 8500 |
| high oleic safflower oil | 1200 |
| MCT oil | 1000 |
| sn2-palmitate oil | 300 |

5. The infant formula of claim 1, wherein said oil blend is a vegetable oil blend.

6. The infant formula of claim 1, wherein the endogenic tocopherol concentration of the oil blend is at most 800 ppm.

7. The infant formula of claim 1, wherein the w/w ratio between alpha tocopherols levels to non-alpha tocopherols levels of the oil blend is at least 5.

8. The infant formula of claim 1, wherein the percentage of diacylglycerol (w/w) of the oil blend is at most 0.5%.

9. The infant formula of claim 1, wherein the w/w ratio of cholesterol present in said formula to phytosterol in said formula is at least 1.

10. The infant formula of claim 2, wherein the w/w ratio of alpha tocopherol levels to non-alpha tocopherols levels is at least 5.

11. The infant formula of claim 2, wherein the percentage (w/w) of diacylglycerol in the oil blend is at most 0.5%.

12. The infant formula of claim 1, wherein said formula comprises at least 5 mg cholesterol/100 g formula.

13. The infant formula according to claim 1 for administration to a subject, wherein the subject is an infant.

14. The infant formula of claim for administration to a subject, wherein said subject is a subject being under partial parenteral nutrition.

15. An infant formula according to claim 1 providing improved stability, improved, wettability, or reduced free fat compared to an infant formula comprising an oil blend of the same oils with higher phytosterol levels.

16. An infant formula accordingly to claim 1 providing increased lipolysis as compared to an infant formula comprising an oil blend of the same oils with higher phytosterol levels.

17. An infant formula according to claim 1 providing increased plasma cholesterol levels or increased absorption of fat soluble vitamins as compared to an infant formula comprising an oil blend of the same oils with higher phytosterol levels.

* * * * *